United States Patent
Ukekawa

(10) Patent No.: US 10,094,822 B2
(45) Date of Patent: Oct. 9, 2018

(54) METHOD FOR SEPARATING BIOTINYLATED NUCLEIC ACID

(71) Applicant: FUJIFILM WAKO PURE CHEMICAL CORPORATION, Osaka-shi, Osaka (JP)

(72) Inventor: Ryo Ukekawa, Amagasaki (JP)

(73) Assignee: FUJIFILM WAKO PURE CHEMICAL CORPORATION, Osaka (JP)

(*) Notice: Subject to any disclaimer, the term of this patent is extended or adjusted under 35 U.S.C. 154(b) by 0 days.

(21) Appl. No.: 15/537,953

(22) PCT Filed: Dec. 17, 2015

(86) PCT No.: PCT/JP2015/085406
§ 371 (c)(1),
(2) Date: Jun. 20, 2017

(87) PCT Pub. No.: WO2016/104338
PCT Pub. Date: Jun. 30, 2016

(65) Prior Publication Data
US 2017/0356902 A1    Dec. 14, 2017

(30) Foreign Application Priority Data

Dec. 22, 2014 (JP) ................. 2014-258324

(51) Int. Cl.
*G01N 33/53* (2006.01)
*C12Q 1/6806* (2018.01)
*C07K 17/14* (2006.01)

(52) U.S. Cl.
CPC .............. *G01N 33/53* (2013.01); *C07K 17/14* (2013.01); *C12Q 1/6806* (2013.01)

(58) Field of Classification Search
CPC .................................................. G01N 33/53
(Continued)

(56) References Cited

U.S. PATENT DOCUMENTS

| 2005/0009002 A1 | 1/2005 | Chen et al. |
| 2005/0089983 A1 | 4/2005 | Takakura |
| 2012/0245331 A1 | 9/2012 | Takakura et al. |

FOREIGN PATENT DOCUMENTS

| EP | 1 381 861 B1 | 1/2010 |
| EP | 2 447 364 B1 | 2/2017 |

(Continued)

OTHER PUBLICATIONS

Milligan et al., "Oligoribonucleotide synthesis using T7 RNA polymerase and synthetic DNA templates," *Nucleic Acids Research*, 15(21): 8783-8798 (1987).

(Continued)

*Primary Examiner* — Jezia Riley
(74) *Attorney, Agent, or Firm* — Leydig, Voit & Mayer, Ltd.

(57) ABSTRACT

An object of the invention is to obtain a biotinylated nucleic acid efficiently, by enhancing dissociation efficiency of biotin in the biotinylated nucleic acid and tamavidin 2 in a tamavidin 2-immobilized insoluble carrier. The inventive method for separating a biotinylated nucleic acid includes (1) contacting a sample containing a biotinylated nucleic acid wherein the biotin is bound to the nucleic acid with a insoluble carrier on which tamavidin is immobilized (a tamavidin-immobilized insoluble carrier) to form a complex of the biotinylated nucleic acid and the tamavidin-immobilized insoluble carrier, and (2) separating the biotinylated nucleic acid from the complex in a solution having pH of 7.8 to 9.5 and in the presence of free biotin. The invention also provides a method for separating the biotinylated nucleic acid to which the nucleic acid-binding protein is bound, a method for separating the nucleic acid-binding protein, and a kit for separating the nucleic acid.

13 Claims, 4 Drawing Sheets
Specification includes a Sequence Listing.

(58) Field of Classification Search
USPC .......................................................... 435/7.5
See application file for complete search history.

(56) References Cited

FOREIGN PATENT DOCUMENTS

| | | |
|---|---|---|
| JP | 2004-528550 A | 9/2004 |
| JP | 2011-055827 A | 3/2011 |
| WO | WO 2002/072817 A1 | 9/2002 |
| WO | WO 2010/150375 A1 | 12/2010 |

OTHER PUBLICATIONS

Takakura et al., "Tamavidin 2-REV: AN engineered tamavidin with reversible biotin-binding capability," *Journal of Biotechnology*, 164(1): 19-25 (20013).

Ukekawa et al., "A Useful New Tool for Isolation of Long Non-coding RNA-binding Proteins," *Medical Science Digest*, 40(7): 355-359 (2014).

Yanai et al., "HMGB proteins function as universal sentinels for nucleic-acid-mediated innate immune responses," *Nature*, 462: 99-103 (2009).

Japanese Patent Office, International Search Report in International Search Report in International Application No. PCT/JP2015/085406 (dated Feb. 9, 2016).

Japanese Patent Office, International Preliminary Examination Report and Written Opinion of the International Searching Authority in International Patent Application No. PCT/JP2015/085406 (dated Jul. 6, 2017).

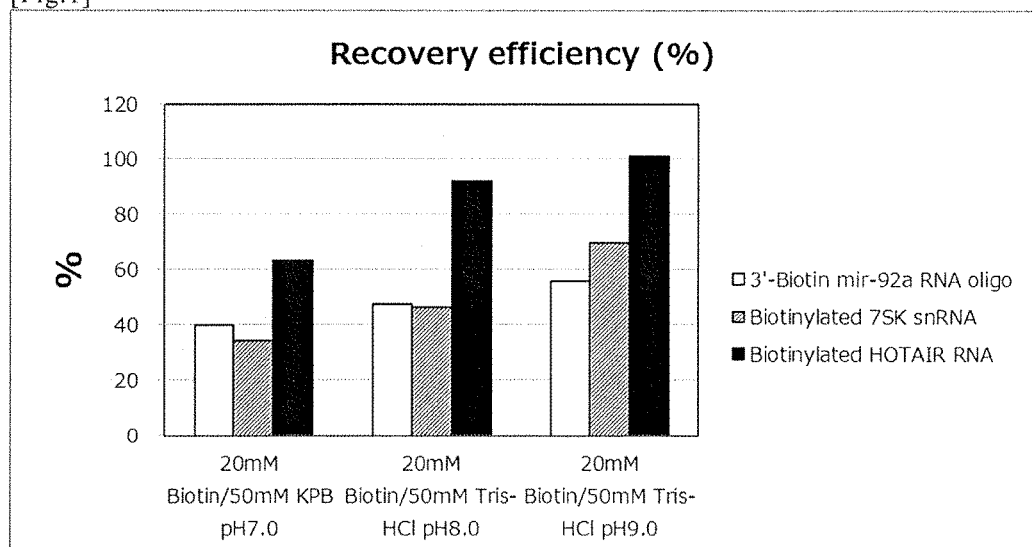
[Fig.1]

[Fig.2]
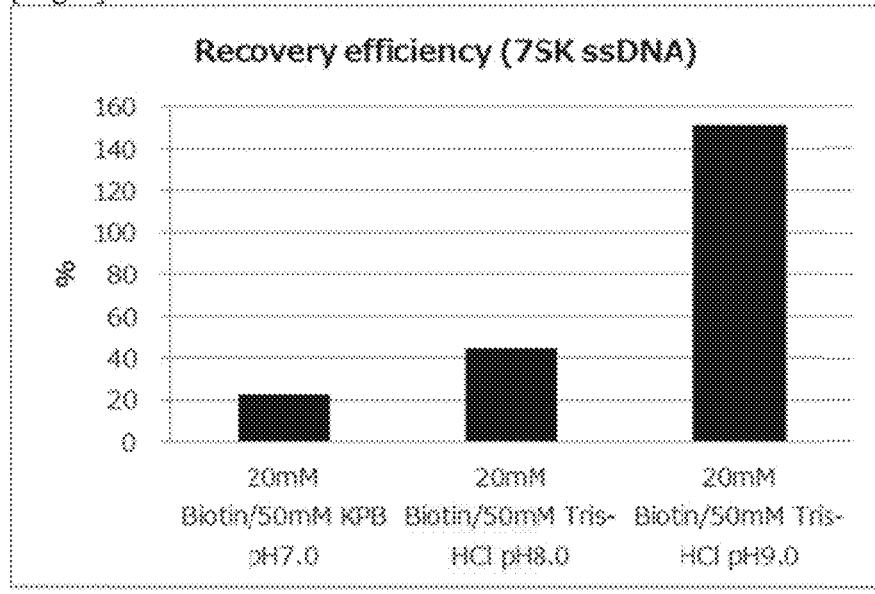
(1)
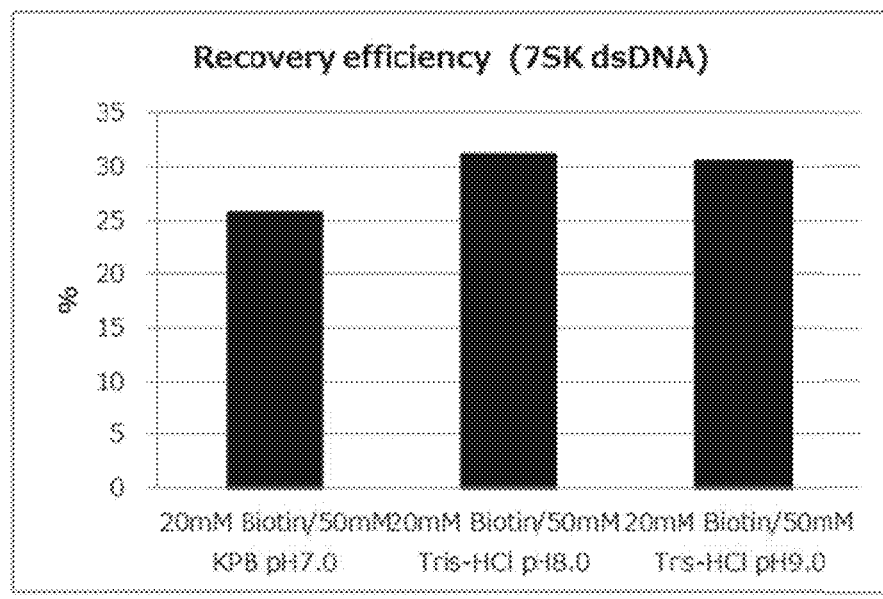
(2)

[Fig.3]
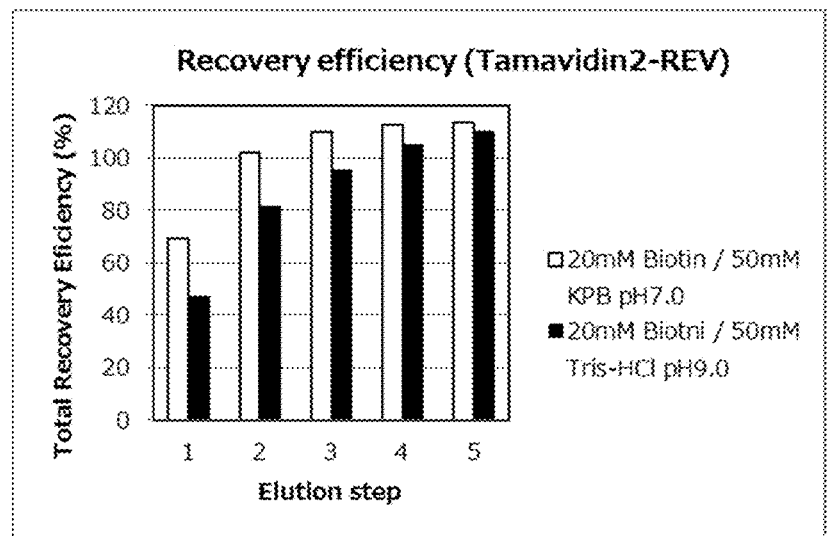
[Fig.4]
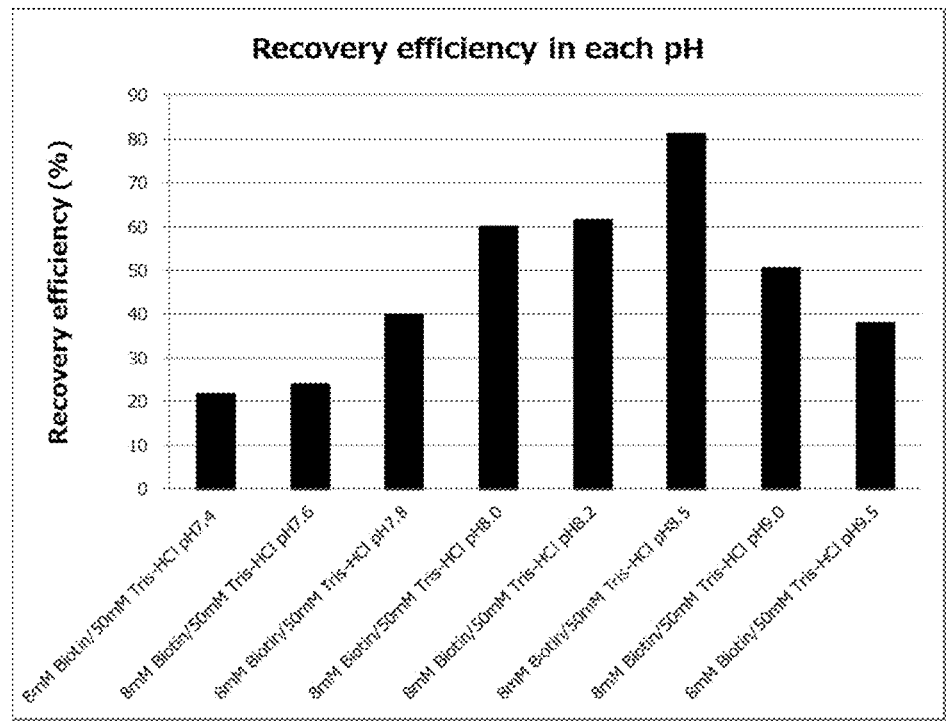

[Fig.5]
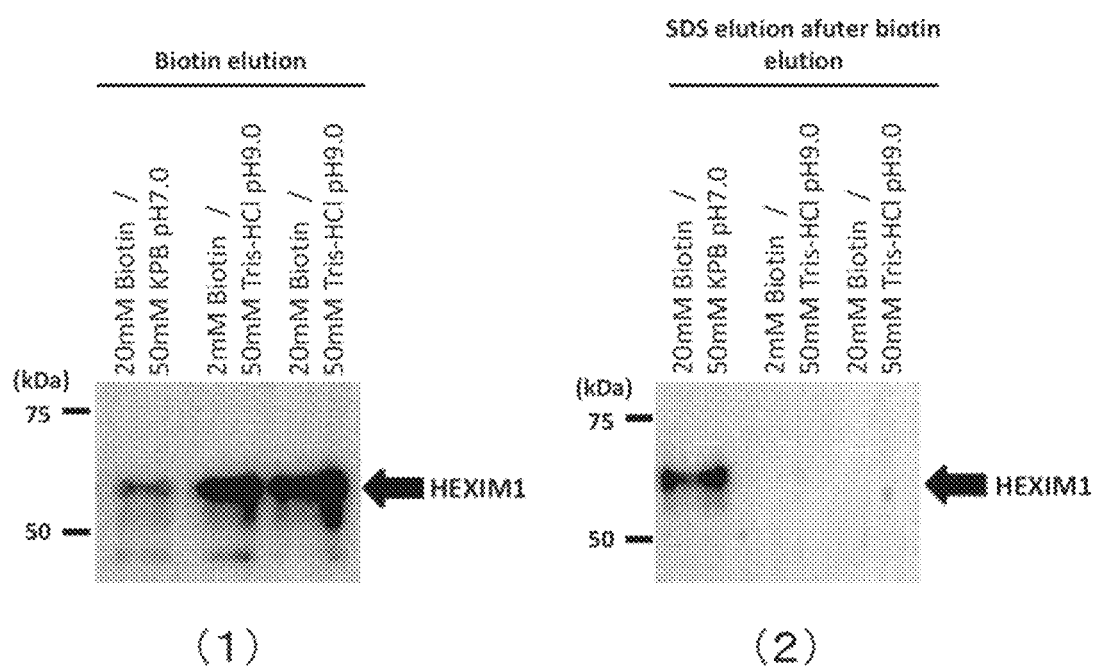

SEQUENCE LISTING

```
<160> NUMBER OF SEQ ID NOS: 4

<210> SEQ ID NO 1
<211> LENGTH: 141
<212> TYPE: PRT
<213> ORGANISM: Artificial Sequence
<220> FEATURE:
<223> OTHER INFORMATION: Synthetic Sequence

<400> SEQUENCE: 1

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ala Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 2
<211> LENGTH: 332
<212> TYPE: DNA
<213> ORGANISM: Artificial Sequence
<220> FEATURE:
<223> OTHER INFORMATION: Synthetic Sequence

<400> SEQUENCE: 2
ggatgtgagg gcgatctggc tgcgacatct gtcaccccat tgatcgccag ggttgattcg      60
gctgatctgg ctggctaggc gggtgtcccc ttcctccctc accgctccat gtgcgtccct     120
cccgaagctg cgcgctcggt cgaagaggac gaccatcccc gatagaggag gaccggtctt     180
cggtcaaggg tatacgagta gctgcgctcc cctgctagaa cctccaaaca agctctcaag     240
gtccatttgt aggagaacgt agggtagtca agcttccaag actccagaca catccaaatg     300
aggcgctgca tgtggcagtc tgcctttctt tt                                   332

<210> SEQ ID NO 3
<211> LENGTH: 2370
<212> TYPE: DNA
<213> ORGANISM: Artificial Sequence
<220> FEATURE:
<223> OTHER INFORMATION: Synthetic Sequence

<400> SEQUENCE: 3
ccagttctca ggcgagagcc gcggctgaca gggtctggga cagaaggaaa gccctccagc      60
```

```
ctccaggccc tgccttctgc ctgcacattc tgccctgatt tccggaacct ggaagcctag    120
gcaggcagtg gggaactctg actcgcctgt gctctggagc ttgatccgaa agcttccaca    180
gtgaggactg ctccgtgggg gtaagagagc accaggcact gaggcctggg agttccacag    240
accaacaccc ctgctcctgg cggctcccac ccgggactta gaccctcagg tccctaatat    300
cccggaggtg ctctcaatca gaaaggtcct gctccgcttc gcagtggaat ggaacggatt    360
tagaagcctg cagtagggga gtggggagtg gagagaggga gcccagagtt acagacggcg    420
gcgagaggaa ggaggggcgt ctttattttt ttaaggcccc aaagagtctg atgtttacaa    480
gaccagaaat gccacggccg cgtcctggca gagaaaaggc tgaaatggag gaccggcgcc    540
ttccttataa gctcgttggg gcctaagcca gtaccgacct ggtagaaaaa gcaaccacga    600
agctagagag agagccagag gagggaagag acgccagac gaaggtgaaa gcgaaccacg    660
cagagaaatg caggcaaggg agcaaggcgg cagttcccgg aacaaacgtg gcagagggca    720
agacgggcac tcacagacag aggtttatgt attttattt tttaaaatct gatttggtgt    780
tccatgagga aagggaaaa tctagggaac gggagtacag agagaataat ccgggtccta    840
gctcgccaca tgaacgccca gagaacgctg gaaaaacctg agcgggtgcc ggggcagcac    900
ccggctcggg tcagccactg ccccacaccg ggcccaccaa gccccgcccc tcgcggccac    960
cggggcttcc ttgctcttct tatcatctcc atctttatga tgaggcttgt taacaagacc   1020
agagagctgg ccaagcacct ctatctcagc cgcgcccgct cagccgagca gcggtcggtg   1080
gggggactgg gaggcgctaa ttaattgatt cctttggact gtaaaatatg gcggcgtcta   1140
cacggaaccc atggactcat aaacaatata tctgttgggc gtgagtgcac tgtctctcaa   1200
ataatttttc cataggcaaa tgtcagaggg ttctggattt ttagttgcta aggaaagatc   1260
caaatgggac caattttagg aggcccaaac agagtccgtt cagtgtcaga aaatgcttcc   1320 ccaaggggt tgggagtgtg ttttgttgga aaaaagcttg ggttatagga aagccttcc    1380 ctgctacttg tgtagaccca gcccaattta agaattacaa ggaagcgaag gggttgtgta   1440
ggccggaagc ctctctgtcc cggctggatg caggggactt gagctgctcc ggaatttgag   1500
aggaacatag aagcaaaggt ccagccttg cttcgtgctg attcctagac ttaagattca    1560
aaaacaaatt tttaaaagtg aaaccagccc tagcctttgg aagctcttga aggttcagca   1620
cccacccagg aatccacctg cctgttacac gcctctccaa gacacagtgg caccgctttt   1680
ctaactggca gcacagagca actctataat atgcttatat taggtctaga agaatgcatc   1740
ttgagacaca tgggtaacct aattatataa tgcttgttcc atacaggagt gattatgcag   1800
tgggaccctg ctgcaaacgg gactttgcac tctaaatata gaccccagct gggacaaaa    1860 gttgcagtag aaaaatagac ataggagaac acttaaataa gtgatgcatg tagacacaga   1920 agggtatt aaaagacaga aataatagaa gtacagaaga acagaaaaaa aatcagcaga    1980
tggagattac cattcccaat gcctgaactt cctcctgcta ttaagattgc tagagaattg   2040
tgtcttaaac agttcatgaa cccagaagaa tgcaatttca atgtatttag tacacacaca   2100
gtatgtatat aaacacaact cacagaatat attttccata cattgggtag gtatgcactt   2160
tgtgtatata taataatgta ttttccatgc agttttaaaa tgtagatata ttaatatctg   2220
gatgcatttt ctgtgcactg gttttatatg ccttatggag tatatactca catgtagcta   2280
aatagactca ggactgcaca ttccttgtgt aggttgtgtg tgtgtggtgg ttttatgcat   2340
aaataaagtt ttacatgtgg tgaatataaa                                    2370
```

```
<210> SEQ ID NO 4
<211> LENGTH: 23
<212> TYPE: RNA
<213> ORGANISM: Homo Sapiens

<400> SEQUENCE: 4
agguugggau cgguugcaau gcu                                              23
```

METHOD FOR SEPARATING BIOTINYLATED NUCLEIC ACID

CROSS-REFERENCE TO RELATED APPLICATIONS

This patent application is the U.S. national phase of International Patent Application No. PCT/JP2015/085406, filed Dec. 17, 2015, which claims the benefit of Japanese Patent Application No. 2014-258324, filed on Dec. 22, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 5,577 bytes ASCII (Text) file named "728944ReplacementSequenceListing.txt," created Aug. 17, 2018.

TECHNICAL FIELD

The present invention relates to a method for separating a biotinylated nucleic acid, which is particularly useful for a research of a nucleic acid-binding protein by pull-down assay.

BACKGROUND ART

Recently, it has become clear that a long non-coding RNA (lncRNA) which does not encode a protein exerts important roles in various life phenomena and thus has attracted attention. In addition, it has also been known that the lncRNA, such as HOTAIR and Xist, will function by binding to a specific protein. From these facts, in analysis of the function of lncRNA, it is an important key to investigate what kind of protein binds to the target lncRNA, and forms a ribonucleoprotein complex (a complex of an RNA and an RNA-binding protein; a RNP complex).

In order to identify the protein which binds to the lncRNA and constitutes the RNP complex, it is necessary to isolate the RNP complex containing the target lncRNA from samples such as cells and tissues. As one of the methods, RNA pull-down assay has been known.

The RNA pull-down assay is a method comprising, synthesizing a biotin-labeled target RNA (for example, lncRNA) by in vitro transcription reaction, subjecting it to a reaction with a sample such as a cell lysate, and then isolating the protein (the RNA-binding protein) interacting with the target RNA as the RNP complex of the RNA-binding protein and the target RNA by using streptavidin beads.

This RNA pull-down assay is an effective technique for carrying out analysis research of the function of lncRNA, since it is capable of isolating the RNP complex, even for the lncRNA where the protein interacting with the RNA is unknown. However, there is a problem in the RNA pull-down assay that there are many cases making difficult to detect only the target RNA-binding protein specifically, because proteins other than the target RNA-binding protein present in the sample also bind nonspecifically to the streptavidin beads.

On the other hand, tamavidin ("TAMAVIDIN" is a registered trademark of Japan Tobacco Inc.) is a novel heat-resistant and avidin-like protein discovered by Japan Tobacco Inc., in an edible mushroom, *Pleurotus cornucopiae*. In addition, tamavidin 2 is a novel avidin-like protein having binding activity to biotin (WO 2002/072817: PATENT LITERATURE 1), similarly as avidin which is a basic protein derived from egg white, or streptavidin derived from Actinomycetes (*Streptomyces avidinii*). Further, tamavidin 2-REV has been developed, which is a modified version of tamavidin 2 obtained by modifying an amino acid sequence of tamavidin 2, and has such extent of binding force that a bonding can be dissociated, while maintaining binding force sufficient to bind to biotinylated substances (PATENT LITERATURE 2, NON-PATENT LITERATURE 1). Furthermore, it has been clarified, in carrying out purification of a biotinylated BSA from *E. coli* lysate using the tamavidin 2-REV immobilized-carrier (NON-PATENT LITERATURE 1), that the biotinylated BSA bound to tamavidin 2-REV immobilized-carrier can be eluted by the addition of a 0.1 M sodium phosphate buffer solution containing excess quantity of biotin (5 mM).

Under such circumstances, the present inventor has considered that a problem in the conventional RNA pull-down assay that proteins other than the target RNA-binding protein are contaminated because of nonspecific protein adsorption to the beads may be solved by carrying out the RNA pull-down assay using tamavidin 2-REV instead of streptavidin, and have carried out the study. As a result, the contamination of nonspecifically adsorbed proteins that causes high background was removed as much as possible, and thus [biotinylated RNA probe to which the RNA-binding protein is bound] could be obtained, when [the biotinylated RNA probe to which the RNA-binding protein is bound] was separated from [the complex of the RNA-binding protein, biotinylated RNA, and tamavidin 2-REV-immobilized magnetic beads] under a mild condition using an elution solution containing excess quantity of biotin (NON-PATENT LITERATURE 2).

CITATION LIST

Patent Literature

PATENT LITERATURE 1: WO 02/072817
PATENT LITERATURE 2: JP A2011-55827

Non-Patent Literature

NON-PATENT LITERATURE 1: Yoshimitsu Takakura, Tamavidin 2-REV: An engineered tamavidin with reversible biotin-binding capability, Journal of Biotechnology, 2013, vol. 164, No. 1, p. 19-25

NON-PATENT LITERATURE 2: Ryo Sheigawa, Takahiro Nishibe, Yoshino, Yoshihusa Sadamura, "Chosa Non-coding RNA Ketugo Proteins no Tnri ni Tekishita Atarashii Kenkyu Tool", Gekkan Medical Science Digest, 2014 June 40 Extra Number (Vol. 524), New Science Co., Ltd. 2014, p. 355-359

NON-PATENT LITERATURE 3: John F. Milligan, et al., Nucleic Acids Research, 1987, vol. 15, No. 21, p. 8783-8798

SUMMARY OF INVENTION

Technical Problem

However, this method using tamavidin 2-REV was not satisfactory in recovery rate of [the biotinylated RNA probe to which the RNA-binding protein is bound]. That is, it was difficult to elute the RNA-binding protein efficiently, in other words, with high recovery rate, since dissociation efficiency of biotin in the biotinylated RNA probe and tamavidin 2 in the tamavidin 2-REV-immobilized magnetic beads was not sufficient.

Therefore, an object of the present invention is to obtain the biotinylated nucleic acid efficiently, by increasing dissociation efficiency of biotin in the biotinylated nucleic acid, and tamavidin 2 in the tamavidin 2-immobilized insoluble carrier.

Solution to Problem

The present invention has been made to solve the problems, and comprises the following constitution.
(1) A method for separating a biotinylated nucleic acid, comprising the following steps:
1) a step for contacting a sample containing a biotinylated nucleic acid wherein the biotin is bound to the nucleic acid with a insoluble carrier on which tamavidin is immobilized (a tamavidin-immobilized insoluble carrier) to form a complex of the biotinylated nucleic acid and the tamavidin-immobilized insoluble carrier (step A-1),
2) a step for separating the biotinylated nucleic acid from the complex obtained in the step A-1, in a solution having pH of 7.8 to 9.5, and in the presence of free biotin (step A-2).
(2) A method for separating a biotinylated nucleic acid to which a nucleic acid-binding protein is bound, comprising the following steps:
1) a step for contacting a sample containing a protein capable of binding to a nucleic acid (a nucleic acid-binding protein), a biotinylated nucleic acid wherein the biotin is bound to the nucleic acid, and a tamavidin-immobilized insoluble carrier to form a complex of the nucleic acid-binding protein, the biotinylated nucleic acid, and the tamavidin-immobilized insoluble carrier (step B-1), 2) a step for separating the biotinylated nucleic acid to which the nucleic acid-binding protein is bound from the complex obtained in the step B-1, in a solution having pH of 7.8 to 9.5, and in the presence of free biotin (step B-2).
(3) A method for separating a nucleic acid-binding protein, comprising the following steps:
1) a step for contacting a sample containing a nucleic acid-binding protein, a biotinylated nucleic acid wherein the biotin is bound to the nucleic acid, and a tamavidin-immobilized insoluble carrier to form a complex of the nucleic acid-binding protein, the biotinylated nucleic acid, and the tamavidin-immobilized insoluble carrier (step C-1),
2) a step for separating the biotinylated nucleic acid to which the nucleic acid-binding protein is bound from the complex obtained in the step C-1, in a solution having pH of 7.8 to 9.5, and in the presence of free biotin (step C-2),
(3) a step for separating the nucleic acid-binding protein from the biotinylated nucleic acid to which the nucleic acid-binding protein is bound obtained in the step C-2 (step C-3).
(4) A kit for separating a nucleic acid, comprising a reagent containing an insoluble carrier on which tamavidin is immobilized, and a reagent which makes pH of the solution after mixing in 7.8 to 9.5, as constituent reagents.

The present inventors have studied extensively to solve the problems, and have discovered, as a result, that the biotinylated nucleic acid is separated efficiently from the complex of the biotinylated nucleic acid and the tamavidin 2-immobilized insoluble carrier, by shifting pH of the solution to an alkaline side of 7.8 to 9.5, in the presence of excess quantity of free biotin relative to the tamavidin, and have thus completed the present invention.

Advantageous Effects of Invention

According to the present invention, the biotinylated nucleic acid can be obtained efficiently and in good accuracy, by using the tamavidin-immobilized insoluble carrier pertaining to the present invention, and by shifting pH of the solution to an alkaline side of 7.8 to 9.5, in the presence of excess quantity of free biotin relative to the tamavidin.

In addition, according to the method of the present invention, the complex of the nucleic acid-binding protein and the biotinylated nucleic acid can be obtained efficiently and in high accuracy. Furthermore, the complex of the unknown nucleic acid-binding protein and the nucleic acid can be isolated, even for the nucleic acid whose binding protein is unknown. From the above, the present invention is also useful for functional analysis of non-coding nucleic acids, or for research of nucleic acid-binding proteins.

BRIEF DESCRIPTION OF DRAWINGS

FIG. 1 shows the results obtained in Example 1, and is a graph comparing recovery efficiency of the biotinylated RNA from the tamavidin 2-REV carrier, using various elution buffers.

FIG. 2 shows the results obtained in Example 2, wherein (1) is a graph showing examination results of recovery efficiency of the biotinylated 7SK ssDNA from the complex of the biotinylated 7SK ssDNA and tamavidin 2-REV-immobilized magnetic beads, using various elution buffers. In addition, (2) is a graph comparing recovery efficiency of the biotinylated 7SK dsDNA from the complex of the biotinylated 7SK dsDNA and the tamavidin 2-REV-immobilized magnetic beads, using various elution buffers.

FIG. 3 shows the results obtained in Comparative Example 1, and is a graph comparing recovery efficiency of tamavidin 2-REV from the biotin carrier not bound to the nucleic acid, using various elution buffers.

FIG. 4 shows the results obtained in Example 3 by carrying out verification for an effective pH range of the elution buffer by comparing recovery efficiency of the biotinylated RNA from the tamavidin 2-REV carrier, using various elution buffers with different pH.

FIG. 5 shows the results of western blotting, obtained in Example 4 by carrying out comparison of elution efficiency of the RNA-binding proteins bound to the biotinylated RNA, from the tamavidin 2-REV carrier in the RNA pull-down assay, using various elution buffers.

DESCRIPTION OF EMBODIMENTS

Hereinafter, in the present description, words "separation" and "dissociation" are not used in particular distinction.

In addition, in the present description, for convenience, a single complex is sometimes shown into one using [ ], as in, for example, [the complex of the biotinylated nucleic acid and the tamavidin-immobilized insoluble carrier].
[Tamavidin]

Tamavidin pertaining to the present invention includes an avidin-like biotin-binding protein obtained from an edible mushroom, *Pleurotus cornucopiae*, and having reversibly binding property to biotin.

Specifically, there are included both
(i) tamavidin 1 disclosed in WO 2002/072817 (PATENT LITERATURE 1) and its modified form, tamavidin 2 disclosed in PATENT LITERATURE 1 and its modified form, or a modified form of tamavidin 2 disclosed in JP A2011-55827 (PATENT LITERATURE 2), and (ii) the one having reversibly binding property to biotin, namely, having binding property to biotin in the biotinylated nucleic acid (the biotin-labeled nucleic acid formed by binding biotin to the nucleic acid; hereinafter meaning is the same as above) in acidic to neutral condition, however, the binding with biotin in the biotinylated nucleic acid dissociates, in the presence of excess quantity of free biotin relative to tamavidin (40 to 4000 times mol relative to tamavidin), and under alkaline condition, preferably under condition of pH 7.8 to pH 9.5.

Among the tamavidin 1, tamavidin 2 and modified forms thereof, TM2 S36A, TM2 D116A, TM2 P46T-T78A, TM2 P46T-D116A, TM2 P46T-T78A-D116A, TM2 T78A, and TM2 T78A-D116A, which are modified forms of tamavidin 2 disclosed in PATENT LITERATURE 2, are preferable. Among them, TM2 S36A is particularly preferable.

An amino acid sequence of the tamavidin 2 pertaining to the present invention is shown as SEQ ID NO: 2 in PATENT LITERATURE 1. An amino acid sequence of TM2 S36A is shown as SEQ ID NO: 4 in PATENT LITERATURE 2. In the present description, the amino acid sequence of TM2 S36A is shown herein as SEQ ID NO: 1. TM2 S36A has such the amino acid sequence that serine at position $36^{th}$ from the N terminus of the amino acid sequence of tamavidin 2 is substituted with alanine.

In the present description, tamavidin 1, tamavidin 2, and modified forms thereof are collectively referred to simply as "tamavidin pertaining to the present invention", or simply as "tamavidin" in some cases. In addition, the tamavidin 2 and modified forms thereof may be abbreviated simply as "tamavidin 2 pertaining to the present invention" in some cases.

In addition, the tamavidin pertaining to the present invention includes the one having the amino acid sequence of the tamavidin pertaining to the present invention, the one having the amino acid sequence of the tamavidin pertaining to the present invention except that one or several amino acids are deleted, substituted or added, or the one having an amino acid sequence having a sequence homology of 70% or more, preferably 80% or more, more preferably 95% or more, and further more preferably 97% or more to the amino acid sequence of tamavidin, and having the property shown in (ii).

Further, the tamavidin pertaining to the present invention includes the one having the amino acid sequence shown in SEQ ID NO: 1 except that one or several amino acids are deleted, substituted, or added, or the one having the amino acid sequence having a sequence homology of 70% or more, preferably 80% or more, more preferably 95% or more, and further more preferably 97% or more to the amino acid sequence shown in SEQ ID NO: 1, and having property shown in (ii).

TM2 S36A is commercially available from Wako Pure Chemical Industries, Ltd., under the trade name of "tamavidin 2-REV". Hereinafter, in the present description, TM2 S36A is described as "tamavidin 2-REV".

In addition, the tamavidin pertaining to the present invention may be a recombinant product produced by genetical methods disclosed in, for example, PATENT LITERATURE 1 or PATENT LITERATURE 2.

Furthermore, the tamavidin pertaining to the present invention may be the commercially available one. For example, tamavidin 2-REV (produced by Wako Pure Chemical Industries, Ltd.) is included.

[Tamavidin-Immobilized Insoluble Carrier]

The tamavidin pertaining to the present invention is used by making immobilized (supported) on the insoluble carrier.

As the insoluble carrier pertaining to the present invention, any carrier can be used, as long as it is usually used in this field. For example, there are included the one prepared by using as a material a natural polymer compound such as cellulose or the derivatives thereof; a synthetic polymer compound, such as polystyrene, polyacrylic acid, polymethacrylic acid, polyacrylamide, polyglycidyl methacrylate, polypropylene, polyvinyl chloride, polyethylene, polychlorocarbonate, a silicone resin, silicone rubber, polyolefin, polyamide, polyimide, polyurethane, and polyester; an inorganic substance, such as porous glass, frost glass, alumina, silica gel, silicon oxide, diatom, activated carbon, and a metal oxide.

In addition, these carriers can be used in a wide variety of forms, such as a particle (a latex particle, a bead, a magnetic beads, and the like), a tube, a carbon nanotube, a chip, a disk-like piece, a fine particle, a thin film, a microtubule, a plate, a microplate, a filters, and the like.

Among these forms, the form of particle is particularly preferable, from the viewpoint of operability.

Among these, a magnetic particle containing a magnetic substance (a magnetic bead), such as a magnetic latex particle (latex particles containing magnetic particles) are more preferable, because these are capable of carrying out B/F separation satisfactorily by using magnetic force. For example, commercially available biochemical magnetic beads (Dynabeads™ (produced by Thermo Fisher Scientific Co., Ltd.), and the like.) are included.

In the case of a particle or a fine particle, a size of the insoluble carrier may be any size, as long as it is easily dispersed in a solution. For example, in the case of a magnetic bead, the diameter thereof is usually 0.1 to 10 µm, preferably 0.1 to 5 µm, and more preferably 1 to 3 µm.

When the insoluble carrier is other than the particle or the fine particle, the size usually used in this field may be selected appropriately, depending on the type of each insoluble carrier.

Immobilization of the tamavidin pertaining to the present invention on the insoluble carrier may be carried out by contacting a tamavidin solution containing tamavidin with the insoluble carrier. In addition, it is also possible to perform the immobilization by a known method for binding a protein to a carrier, for example, by a method for immobilization by covalent bonding, a method for immobilization by physical adsorption, or the like. A specific immobilization method may be selected appropriately, depending on the type of the insoluble carrier, or the like.

For example, the tamavidin-immobilized magnetic beads can be prepared easily by contacting the magnetic beads with a tamavidin solution (for example, by immersing the magnetic beads in a tamavidin aqueous solution) for about 1 to 6 hours, and preferably about 3 to 5 hours.

When the commercially available magnetic beads are used, the tamavidin pertaining to the present invention may be immobilized on the magnetic beads, according to a protocol attached to the product.

An amount of the tamavidin to be supported on the insoluble carrier varies depending on the type of the insoluble carrier. When the insoluble carrier is particles or fine particles, it is usually 0.5 to 2000 µg, and preferably 2 to 500 µg, relative to 1 mg of the insoluble carrier. When the insoluble carrier is the magnetic beads, an amount of tamavidin to be immobilized on the magnetic beads is usually 0.5 to 200 μg, preferably 2 to 100 μg, and more preferably 20 to 80 μg, relative to 1 mg of the magnetic beads.

When the insoluble carrier is other than particles or fine particles, an amount of tamavidin to be supported on the carrier may be adjusted appropriately, depending on the type of each insoluble carrier.

After immobilization of the tamavidin pertaining to the present invention on the insoluble carrier, it is separated from a tamavidin solution by an arbitrary method. As a method for separating the insoluble carrier, an arbitrary method, such as decantation, centrifugation, and filter separation, may be used, depending on the type of the insoluble carrier used. In the case of using the magnetic beads, it is possible to easily separate the tamavidin-immobilized magnetic beads from the tamavidin solution by a magnetic separation method.

Although the tamavidin-immobilized insoluble carrier pertaining to the present invention can be prepared by a method known per se as described above, a commercially available product of the insoluble carrier on which the tamavidin pertaining to the present invention is immobilized may be used. For example, MagCapture™ Tamavidin™ 2-REV (produced by Wako Pure Chemical Industries, Ltd.) is included.

[Nucleic Acid]

The nucleic acid pertaining to the present invention to be used for the biotinylated nucleic acid wherein biotin is bound to a nucleic acid may be a deoxyribonucleic acid (DNA) or a ribonucleic acid (RNA), and is not especially limited.

The nucleic acid is preferably a single strand.

In addition, the type of the nucleic acid pertaining to the present invention is not especially limited, and it is included, for example, the nucleic acid having binding property to the nucleic acid-binding protein as described in explanation concerning (step B-1) described below, to form the complex with the nucleic acid-binding protein. For example, in the case of the RNA, a non-translatable RNA (non-coding RNA: ncRNA) which does not encode a protein in vivo is included as an example thereof.

As for the non-coding RNA, for example, there is included the long-chain non-coding RNA (long non-coding RNA: lncRNA) having a chain length of 200 bases or more; a small RNA (small RNA, miRNA or the like.) having a total length of about 5 bases to 200 bases or less, such as a microRNA (miRNA), a small interfering RNA (siRNA), a small nuclear RNA (snRNA), a small nucleolar RNA (snoRNA), a repeat associated small interfering RNA (rasiRNA), a trans-acting siRNA (tasiRNA), and a PIWI interacting RNA (piRNA).

As for lncRNA, for example, HOTAIR RNA is included. The small nuclear RNA includes, for example, 7SK snRNA.

In the case of the DNA, a gene-expression regulatory region (base sequence thereof, or the like) to which a transcription factor or an enhancer binds, or the like, is included.

In addition, the nucleic acid pertaining to the present invention encompasses such a nucleic acid that presence of protein which binds to the nucleic acid is unknown.

[Biotinylated Nucleic Acid]

The biotinylated nucleic acid pertaining to the present invention can be obtained by binding the nucleic acid pertaining to the present invention to biotin to biotinylate (to label with biotin).

The method for labeling the nucleic acid with biotin includes usual methods, such as in vitro transcription reaction (NON-PATENT LITERATURE 3), an enzymatic labeling method using Terminal Deoxynucleotidyl Transferase (TdT), or the like, a method for introducing biotin to the 5' terminal of the nucleic acid using biotin phosphoramidite during DNA synthesis, a method for end labeling by PCR using a biotinylated primer, a method for chemical biotinylation using biotin-X-NHS Ester™, a method in which a double-stranded DNA is labeled enzymatically by a Klenow DNA polymerase, nick translation or a mixed primer labeling method, and it is not limited thereto. It may be selected appropriately depending on the type of the target nucleic acid to be labeled with biotin. Generally, the in vitro transcription reaction is often carried out.

An amount of biotin to be bound to the nucleic acid is 5 pmol to 100 pmol, preferably 15 pmol to 50 pmol, and more preferably 20 pmol to 30 pmol.

In addition, the biotinylated nucleic acid can also be obtained by contract manufacturing to a vendor.

Hereinafter, a method for producing the biotinylated RNA using the in vitro transcription reaction is exemplified.

The DNA having a gene sequence encoding the target RNA is incorporated into a vector (cloned), by utilizing a restriction enzyme site of the vector (having a promoter site, such as a T7 promoter, and an Sp6 promoter, near the restriction enzyme site). Using a recombinant DNA portion of the obtained recombinant vector as a template, a PCR amplification reaction is carried out using, for example, the T7 primer and the Sp6 primer to amplify the gene sequence of the RNA. Regarding the obtained PCR amplification products, ordinary electrophoresis such as agarose electrophoresis, and gel extraction and purification are carried out to purify the PCR amplification products containing a gene sequence of the target RNA and the T7 promoter sequence and the Sp6 promoter sequence.

As a vector into which the gene sequence of the target RNA is incorporated, the vector capable of incorporating the gene sequence of the target RNA, and the one having a promoter site, such as the T7 promoter, the Sp6 promoter, and the T3 promoter near the restriction site to be incorporated is preferable, because of easy handling. A commercially available product includes, for example, a pGEM-T Easy vector (Promega Corporation), a pBluescript II SK (+/−) (Stratagene Corporation), or the like.

Using the obtained PCR amplification product as a template, RNA synthesis is carried out by the in vitro transcription reaction according to a usual method. Since a kit for carrying out RNA synthesis (for example, a MEGAscript™ T7 Transcription Kit, produced by Thermo Fisher Scientific Inc.) is commercially available, RNA synthesis may be carried out using it. As a nucleotides to be used as a substrate in RNA synthesis, ATP, GTP, CTP, and a mixture of UTP and Biotin-16-UTP (produced by Roche Diagnostics K. K.) at a molar ratio of 3:1 are used. By doing so, the biotinylated RNA can be obtained. Then, the obtained biotinylated RNA is purified by a usual method.

[A. Method for Separating Biotinylated Nucleic Acid of the Present Invention]

The method for separating the biotinylated nucleic of the present invention acid comprises the following steps:

"(1) a step for contacting a sample containing the biotinylated nucleic acid with the tamavidin-immobilized insoluble carrier to form a complex of the biotinylated nucleic acid and the tamavidin-immobilized insoluble carrier (step A-1), (2) a step for separating the biotinylated nucleic acid from the complex obtained in the step A-1, in a solution having pH of 7.8 to 9.5, and in the presence of free biotin (step A-2)."

(Step A-1)

Step A-1 of the method of the present invention for separating the biotinylated nucleic acid is "a step for contacting a sample containing the biotinylated nucleic acid with the tamavidin-immobilized, insoluble carrier to form a complex of the biotinylated nucleic acid and the tamavidin-immobilized insoluble carrier".

The sample containing the biotinylated nucleic acid in the step A-1 is the one containing the biotinylated nucleic acid where the nucleic acid pertaining to the present invention is biotinylated, and it is used in a solution state, in the step A-1.

A solvent to be used for preparation of the solution containing the biotinylated nucleic acid includes RNase-free ultrapure water or an RNase-free buffer solution. The buffer solution is not especially limited, as long as it is the one usually used in this field, and includes the one having buffering action at near neutral pH of usually pH 6.0 to 8.5, preferably pH 7.0 to 8.0, and more preferably pH 7.0 to 7.5. Specifically, there is included, for example, phosphate buffered saline (PBS), HEPES buffer solution, borate buffer solution, Tris buffer solution, phosphate buffer solution, veronal buffer solution, Good's buffer solution, or the like. In addition, concentration of the buffering agent of these buffer solutions is selected appropriately from a range of usually 10 to 100 mM, and preferably 10 to 50 mM.

Concentration of the biotinylated nucleic acid in the reagent solution in which the biotinylated nucleic acid is suspended in the solvent described above may be such concentration that provides an objective concentration range when it was mixed with the tamavidin-immobilized insoluble carrier or a solution containing the carrier. It is, for example, 1 to 100 ng/μL, preferably 1 to 50 ng/μL, and more preferably 10 to 50 ng/μL.

The pH of the solution containing the biotinylated nucleic acid is preferably about 6.0 to 8.0, in consideration of stability of the biotinylated nucleic acid.

It should be noted that, the solution containing the biotinylated nucleic acid may further contain sensitizer, surfactant, preservative (for example, sodium azide, salicylic acid, benzoic acid), stabilizer (for example, albumin, globulin, water-soluble gelatin, surfactant, saccharides), activator, effect avoiding agent of coexisting substances, or the like, and others, which are usually used in this field and do not inhibit/suppress the reaction of forming the complex of the biotinylated nucleic acid and the tamavidin-immobilized insoluble carrier. In addition, a concentration range of these reagents, or the like, may be selected and used appropriately from a usually used range in the measurement method known per se.

The tamavidin-immobilized insoluble carrier to be used in the step A-1 may be in a form of a solution suspended in a solvent (suspension) (hereinafter referred to as "the tamavidin-immobilized insoluble carrier solution"), or may be in a form of a pellet from which the solution is removed. In use in the form of the solution, the solvent for suspending the tamavidin-immobilized insoluble carrier is not especially limited, as long as it is the one usually used in this field, and there are included the buffer solutions having buffering action at near neutral pH of usually pH 6.0 to 8.5, and preferably pH 7.0 to 8.0. Specifically, there is included, for example, phosphate buffered saline (PBS), HEPES buffer solution, borate buffer solution, Tris buffer solution, phosphate buffer solution, veronal buffer solution, Good's buffer solution, or the like. In addition, concentration of the buffering agent of these buffer solutions is selected appropriately from a range of usually 10 to 100 mM, and preferably 10 to 50 mM.

Concentration of the tamavidin in the tamavidin-immobilized insoluble carrier solution as described above may be such concentration that provides an objective concentration range when mixed with a solution containing the biotinylated nucleic acid. It is, for example, 0.01 mM to 0.2 mM, preferably 0.02 mM to 0.1 mM, more preferably 0.02 mM to 0.05 mM, and further preferably 0.03 mM to 0.05 mM.

In addition, an content of the insoluble carrier in the tamavidin-immobilized insoluble carrier solution varies depending on the kind of the carrier to be used, and when the carrier is particles such as magnetic beads, it is usually 0.05 mg to 10 mg, preferably 0.1 mg to 1 mg, and further preferably 0.2 mg to 0.5 mg.

In addition, pH of the solution containing the tamavidin-immobilized insoluble carrier solution is preferably about pH 6.0 to 8.0, in consideration of stability of the tamavidin-immobilized insoluble carrier.

It should be noted that, the tamavidin-immobilized insoluble carrier solution may further contain sensitizer, surfactant, preservative (for example, sodium azide, salicylic acid, benzoic acid), stabilizer (for example, albumin, globulin, water-soluble gelatin, surfactant, saccharides), activator, effect avoiding agent of coexisting substances, or the like, and others, which are usually used in this field and do not inhibit/suppress the reaction of forming the complex of the biotinylated nucleic acid and the tamavidin-immobilized insoluble carrier. In addition, a concentration range, or the like, of these reagents may be selected and used appropriately, from a usually used range in the measurement method known per se.

In the step A-1, the method for contacting the sample containing the biotinylated nucleic acid with the tamavidin-immobilized insoluble carrier is selected appropriately depending on the type of the insoluble carrier to be used, and may be such a method that finally [the complex of the biotinylated nucleic acid and the tamavidin-immobilized insoluble carrier] or a solution of the complex is obtained.

For example, when the insoluble carrier is the particle or the fine particle, there is included a method of mixing the sample containing the biotinylated nucleic acid with the tamavidin-immobilized insoluble carrier, or a method of mixing the sample containing the biotinylated nucleic acid with a solution containing the tamavidin-immobilized insoluble carrier solution.

When the insoluble carrier is the chip, the plate, or the like, the insoluble carrier on which the tamavidin of the present invention is immobilized and the sample containing the biotinylated nucleic acid may be contacted. The method for immobilizing tamavidin on the insoluble carrier includes a common method usually used in this field.

In the step A-1, when the sample containing the biotinylated nucleic acid is contacted and reacted with the tamavidin-immobilized insoluble carrier, concentration of the biotinylated nucleic acid in the reaction solution is, for example, 0.1 to 100 ng/μL, preferably 0.5 to 50 ng/μL, and more preferably 1 to 20 ng/μL.

In the step A-1, when the sample containing the biotinylated nucleic acid is contacted and reacted with the tamavidin-immobilized insoluble carrier, concentration of the tamavidin in the reaction solution varies depending on the concentration of the biotinylated nucleic acid in the sample, and is not especially limited, and it is usually 0.001 mM to 0.2 mM.

In the step A1, when the sample containing the biotinylated nucleic acid is contacted and reacted with the tamavidin-immobilized insoluble carrier, a content of the tamavidin-immobilized insoluble carrier in the reaction solution varies depending on the type of the carrier to be used, and when the insoluble carrier is the particles or the fine particles, it is usually 0.001 to 10 mg, and preferably 0.005 to 5 mg. When the insoluble carrier is the magnetic beads particles, it is usually 0.05 to 10 mg, and preferably 0.1 to 1 mg.

In addition, when the sample containing the biotinylated nucleic acid is contacted and reacted with the tamavidin-immobilized insoluble carrier, pH of the reaction solution is not especially limited, as long as it is in a range not inhibiting/suppressing the reaction of forming the complex of the biotinylated nucleic acid and the tamavidin-immobilized insoluble carrier, and includes a range from 4.0 to 8.0, and preferably from 7.0 to 7.5.

Temperature at the time of reaction is also not especially limited, as long as it is in a range not inhibiting/suppressing the reaction of forming the complex and not separating the complex formed, and includes a range usually 3 to 50° C., and preferably 3 to 25° C. In addition, the reaction time varies depending on the reaction conditions, such as the type of the biotinylated nucleic acid and the tamavidin-immobilized insoluble carrier to be used, pH, and temperature, and it is about 0.1 to 24 hours, and preferably about 1 to 5 hours. During the reaction, stirring treatment may be carried out, as necessary.

After the reaction in the step A-1, it is preferable to separate [the complex of the biotinylated nucleic acid and the tamavidin-immobilized insoluble carrier] from the obtained reaction solution. The method is selected appropriately depending on the type of the insoluble carrier to be used. For example, a conventional method such as decantation, centrifugation, and filter separation, may be carried out. When the magnetic beads are used as the insoluble carrier, the magnetic beads and the solution can be separated using a magnet.

Furthermore, it is preferable to wash the obtained insoluble carrier using an appropriate washing solution, in order to remove contaminants adhered to the insoluble carrier of the complex. The washing solution includes a buffer solution, or the like, usually used in this field. For example, PBS or a buffer solution having buffering action at near neutral pH of pH of 6.0 to 7.5 is preferable. Furthermore, the washing solution may contain a surfactant, a salt such as NaCl and $MgCl_2$, usually used in this field.

(Step A-2)

Step A-2 of the method for separating the biotinylated nucleic acid of the present invention is "a step for separating the biotinylated nucleic acid from the complex obtained in the step A-1, in a solution having pH of 7.8 to 9.5, and in the presence of free biotin".

Free biotin pertaining to the present invention means biotin which is not bound to the nucleic acid and exists in a free state in a solution.

In step A-2, [the complex of the biotinylated nucleic acid and the tamavidin-immobilized insoluble carrier] obtained in the step A-1 is contacted and subjected to a reaction with free biotin in a solution state of pH 7.8 to pH 9.5.

The method may be any method, as long as the solution containing the complex and free biotin, and having pH of 7.8 to 9.5 can be obtained.

For example, the following methods are included.

(1) A method for mixing [the complex of the biotinylated nucleic acid and the tamavidin-immobilized insoluble carrier] or the solution containing the complex with the solution containing free biotin, and then mixing with a solution which makes pH of the solution after mixing in 7.8 to 9.5, (2) a method for mixing the complex or the solution containing the complex with a solution which makes pH of the solution after mixing in 7.8 to 9.5, and then mixing with the solution containing free biotin, (3) a method for mixing the complex or the solution containing the complex with a solution which contains free biotin and makes pH of the solution after mixing in 7.8 to 9.5.

Among the methods of (1) to (3), the method of (3) is the most convenient and simple, in consideration of work efficiency, or the like.

In particular, a method according to (3), and a method comprising removing the solvent from the solution containing [the complex of the biotinylated nucleic acid and the tamavidin-immobilized insoluble carrier] obtained in the step A-1 by a method depending on property of the insoluble carrier, and then mixing the complex with the solution which contains free biotin and makes pH of the solution after mixing in 7.8 to 9.5 is simple and easy.

In this case, the solution to be used may be a solution having pH of 7.8 to 9.5, because the solvent is removed, and then the complex is mixed with a solution which makes pH of the solution after mixing in 7.8 to 9.5.

A solvent to be used for the solution containing [the complex of the biotinylated nucleic acid and the tamavidin-immobilized insoluble carrier] pertaining to the step A-2 includes, for example, the same solvent as the solvent for suspending the tamavidin-immobilized insoluble carrier described in the step A-1, and, it is not especially limited.

The solvent to be used for preparing the solution containing free biotin to be used in the step A-2 includes, for example, potassium phosphate buffer solution, Tris buffer solution, phosphate buffered saline (PBS), HEPES buffer solution, borate buffer solution, phosphate buffer solution, veronal buffer solution, Good's buffer solution, or the like. In addition, concentration of the buffering agent of these buffer solutions is selected appropriately from a range of usually 10 to 1000 mM, and preferably 10 to 100 mM.

Concentration of free biotin in the solution containing free biotin may be such concentration to be excess quantity, so that the complex can be separated into the biotinylated nucleic acid and the tamavidin-immobilized insoluble carrier at pH 7.8 to 9.5, when mixed with [the complex of the biotinylated nucleic acid and the tamavidin-immobilized insoluble carrier], or when mixed with the solution containing the complex. Specifically, it is such concentration that provides 40 to 4000 times mol relative to the tamavidin supported on the insoluble carrier of the complex in the mixed solution, when mixed with [the complex of the biotinylated nucleic acid and the tamavidin-immobilized insoluble carrier], or when mixed with the solution containing the complex. For example, it is such concentration that provides 2 to 40 mM relative to 0.01 to 0.05 mM tamavidin supported on the insoluble carrier of the complex in a mixed solution. About 100 to 4000 times mol is more preferable.

The solution containing free biotin may further contain sensitizer, surfactant, preservative (for example, sodium azide, salicylic acid, benzoic acid, or the like.), stabilizer (for example, albumin, globulin, water-soluble gelatin, surfactant, saccharides, or the like.), activator, effect avoiding agent of coexisting substances, or the like, and others, which are usually used in this field. In addition, a concentration range of these reagents, or the like, may be selected and used appropriately, from a usually used range in the measurement method known per se.

A solution to be used in the step A-2 which makes pH of the solution after mixing in 7.8 to 9.5, includes, for example, a buffer solution having buffering action at near pH 7.8 to pH 9.5, and specifically includes, for example, potassium phosphate buffer solution, Tris buffer solution, phosphate buffer solution, veronal buffer solution, Good's buffer solution, phosphate buffered saline (PBS), HEPES buffer solution, borate buffer solution, or the like. In addition, concentration of the buffering agent of these buffer solutions is selected appropriately from a range of usually 10 to 1000 mM, and preferably 10 to 100 mM.

In the case of using [the complex of the biotinylated nucleic acid and the tamavidin-immobilized insoluble carrier] which is not in a solution state in the step A-2, and in the case where the step A-2 is the method (3) for mixing the complex with the solution which contains free biotin and makes pH after mixing in 7.8 to 9.5, a buffer solution having buffering action at near pH 7.8 to 9.5 may be used as a solution which makes pH after mixing in 7.8 to 9.5.

It should be noted that, in this description, the solution which makes pH after mixing in 7.8 to 9.5, or the solution which contains free biotin and makes pH after mixing in 7.8 to 9.5, may sometimes be referred to as "an elution buffer".

Concentration of free biotin in the reaction solution when the complex is contacted and reacted with free biotin at pH 7.8 to pH 9.5 in the step A-2 is about 40 to 4000 times mol relative to concentration of tamavidin in the reaction solution, that is, relative to the tamavidin supported on the insoluble carrier in the reaction solution, because the use of too high concentration of free biotin will be waste of biotin. In addition, pH of the reaction solution is 7.8 to 9.5.

In the step A-2, when the complex is contacted and reacted with free biotin at pH 7.8 to pH 9.5, reaction temperature includes usually a range of 3° C. to 50° C., and preferably 3° C. to 25° C. In addition, reaction time thereof is for about 1 minute to 360 minutes, preferably for about 10 minutes to 180 minutes, and more preferably for about 10 to 30 minutes in response to each reaction condition, because it varies depending on the reaction conditions, such as the type of the biotinylated nucleic acid to be used, the type of the tamavidin-immobilized insoluble carrier, pH and temperature. During the reaction, stirring treatment may be carried out, as necessary.

It should be noted that, in the case where the nucleic acid in the biotinylated nucleic acid is the RNA, the RNA may cause denaturation, when pH of the solution at the time of separation of the biotinylated nucleic acid from the complex in the step A-2 becomes an alkaline side of pH 9.5 or higher. When the nucleic acid in the biotinylated nucleic acid is the DNA, there is no worry of denaturation, even under such an alkaline condition as pH 9.5 or higher.

However, when the biotinylated DNA is separated under an alkaline condition of pH 9.5 or higher, the work may become complicated, because, in such a case, neutralization treatment of the solution or the like may be required in consideration of the subsequent work (such as the case of using the biotinylated nucleic acid). In addition, in carrying out the present invention using an automated analyzer, it is not preferable to carry out the present invention under too highly alkaline condition, because it is not easy to handle. Furthermore, the protein may be denatured under highly alkaline condition, depending on the type of the nucleic acid-binding protein.

Therefore, also in both cases where the biotinylated nucleic acid is the RNA and the DNA, pH in the step A-2 is preferably pH 7.8 to 9.5, more preferably pH 8.0 to 9.0, and further preferably pH 8.2 to 8.8. The pH of around 8.5 is particularly preferable.

As an example of the method for separating the biotinylated nucleic acid of the present invention, the case where the step A-2 is the method of the (3) (a method for mixing the complex or the solution containing the complex with a solution which contains free biotin and makes pH of the solution after mixing in 7.8 to 9.5) will be specifically explained as follows.

Into a tube, 0.05 to 1 mg of the tamavidin 2-REV-immobilized magnetic beads (supported amount of tamavidin is 0.5 to 2000 µg, 0.3 nM to 1.3 µM, relative to 1 mg of the magnetic beads) is added, and after washing process, the washing solution is removed. Next, the solution containing 10 to 50 ng/µL of the biotinylated RNA is added and reacted under stirring, usually at 3 to 50° C., preferably 3 to 25° C., for 0.1 to 24 hours, preferably 1 to 5 hours, to form the complex of the biotinylated RNA and the tamavidin 2-REV-immobilized magnetic beads. After the reaction, the magnetic beads and the solution are separated using a magnetic stand. After washing the beads several times, the washing solution is removed. Next, 15 to 40 µL of an elution buffer (50 mM Tris-HCl, pH 9.0, containing 5 to 20 mM biotin) is added to the tube, and reacted under stirring, usually at 3 to 50° C., preferably 3 to 25° C., for 1 to 360 minutes, preferably 10 to 180 minutes, and more preferably 10 to 30 minutes. After the reaction, the eluate containing the biotinylated nucleic acid separated from the complex is separated and recovered by using a magnetic stand. The biotinylated nucleic acid can be separated by the above operation.

By carrying out the step A-2, [the complex of the biotinylated nucleic acid and the tamavidin-immobilized insoluble carrier] is reacted with 40 to 4000 times mol of free biotin relative to the tamavidin, in the solution having pH of 7.8 to 9.5, the biotinylated nucleic acid is separated from the complex.

Subsequently, the solution containing the biotinylated nucleic acid can be easily obtained, by separating the biotinylated nucleic acid and the tamavidin-immobilized insoluble carrier which are present separately in the solution, by a usual method depending on the type of the insoluble carrier used. For example, when the magnetic beads are used as the insoluble carrier, the solution containing the biotinylated nucleic acid can be obtained by separating the tamavidin-immobilized magnetic beads by magnetic isolation.

The solution containing the biotinylated nucleic acid may be recovered plural times, by carrying out several times of separation step of the biotinylated nucleic acid remaining on the tamavidin-immobilized insoluble carrier, by adding the solution containing free biotin and the solution which makes pH of the solution after mixing in 7.8 to 9.5, to the tamavidin-immobilized insoluble carrier or the solution containing the carrier after separation of the biotinylated nucleic acid and the tamavidin-immobilized insoluble carrier, or by adding the solution which contains free biotin and makes pH of the solution after mixing in 7.8 to 9.5, to the tamavidin-immobilized insoluble carrier or the solution containing the carrier after separation of the biotinylated nucleic acid and the tamavidin-immobilized insoluble carrier.

If necessary, the biotinylated nucleic acid may also be recovered from the solution containing the biotinylated nucleic acid obtained in the step A-2, by further purification of the nucleic acid by a known nucleic acid extraction method, or the like. For example, a method for phenol/chloroform extraction, or a method using a commercially available nucleic acid purification kit, or the like, is included.

It has been known that binding between biotin and tamavidin 2-REV is separated (dissociated) by adding excess quantity of free biotin. In addition, it has been known that, binding between biotin in the biotinylated protein and tamavidin 2-REV in the tamavidin 2-REV-immobilized insoluble carrier is cleaved to obtain the biotinylated protein by adding excess quantity of free biotin to the complex of the biotinylated protein and the tamavidin 2-REV-immobilized insoluble carrier, by utilizing of this property (NON-PATENT LITERATURE 1). However, binding between the biotinylated nucleic acid and tamavidin 2-REV could not be sufficiently cleaved only by adding excess quantity of free biotin, in the case of using the biotinylated nucleic acid instead of the biotinylated protein.

In this step A-2 of the present invention, dissociation efficiency between the biotinylated nucleic acid to which the nucleic acid-binding protein is bound and the tamavidin-immobilized insoluble carrier is enhanced, and thus the biotinylated nucleic acid can be recovered in good yield, by adjusting pH of the solution containing the complex to 7.8 to 9.5, in the presence of excess quantity of free biotin (40 to 4000 times mol of free biotin relative to the tamavidin pertaining to the present invention).

[B. Method for Separating Biotinylated Nucleic Acid to which Nucleic Acid-Binding Protein is Bound of the Present Invention]

The method for separating the biotinylated nucleic acid to which a nucleic acid-binding protein is bound comprises the following steps:

(1) a step for contacting a sample containing the nucleic acid-binding protein, the biotinylated nucleic acid, and the tamavidin-immobilized insoluble carrier to form a complex of the nucleic acid-binding protein, the biotinylated nucleic acid, and the tamavidin-immobilized insoluble carrier (step B-1), (2) a step for separating the biotinylated nucleic acid to which the nucleic acid-binding protein is bound from the complex obtained in the step B-1, in a solution having pH of 7.8 to 9.5, and in the presence of free biotin (step B-2).

(Step B-1)

The step B-1 for separating the biotinylated nucleic acid to which the nucleic acid-binding protein is bound of the method of the present invention, is "a step for contacting a sample containing the nucleic acid-binding protein, the biotinylated nucleic acid, and the tamavidin-immobilized insoluble carrier to form the complex of the nucleic acid-binding protein, the biotinylated nucleic acid, and the tamavidin-immobilized insoluble carrier".

The nucleic acid-binding protein is not especially limited, as long as it is the protein capable of binding to the nucleic acid pertaining to the present invention. The double-stranded DNA-binding protein, the single-stranded DNA-binding protein, the RNA-binding protein, or the like, is included.

Specifically, there are include, for example, transcription factors or histones, splicing factors or transporters, ribosomal proteins, small nuclear ribonucleoproteins (snRNP proteins), small nucleolar ribonucleoproteins (snoRNP proteins), and the like.

In addition, the HOTAIR RNA has been known to bind to Ezh2 which is a constitutive factor of the Polycomb repressive complex PRC2, and LSD1 of an LSD1/CoREST/REST complex, and the 7SK snRNA has been known to bind to the RNA-binding protein, such as Hexim 1/2, CDK 9, and Larp 7. These RNA-binding proteins are also included as the nucleic acid-binding protein pertaining to the present invention.

The sample containing the nucleic acid-binding protein pertaining to the step B-1 includes a solution in which the nucleic acid-binding protein is dissolved in an appropriate solvent, a cell lysate (cell extract), a cell culture supernatant, body fluids such as plasma, serum, urine, saliva, and breast milk, or a solution obtained by dissolving or suspending them in a solvent.

As the cell lysate, the one in which usually $5\times10^6$ to $2\times10^7$ cells contained in 1 mL of a solution and then lysed, or the one in which $5\times10^6$ to $2\times10^7$ cell pellets are lysed, are used.

As a method to obtain the cell lysate, any method usually carried out to destroy the cell in this field may be used, and a method for chemically solubilizing the cells is more preferable than a method for physically crushing the cells, from the view point that the protein is not thermally denatured, the protein is not inactivated, the protein recovery is good, operation is simple, or the like. For example, a method for solubilizing the cells using a surfactant is preferable.

For example, a cell lysing agent containing a surfactant is added to $5\times10^6$ to $5\times10^7$ cell pellets, and the cells are suspended and then subjected to a reaction on ice for 1 to 10 minutes. Thereafter, the suspension is subjected to centrifugation treatment at 20000×G for about 15 minutes, and the obtained supernatant solution may be used as the cell lysate.

As the cell lysing agent, for example, a buffer solution containing an appropriate salt (KCl, NaCl, or the like) or a reducing agent such as DTT, added with a surfactant as the cell lysing agent usually used in this field, is used. As for the buffer solution, for example, a buffer solution having buffering action at near neutral pH of pH 5.0 to 10.0, and preferably pH 7.0 to 8.0, for example, phosphate buffer solution, Tris buffer solution, Good's buffer solution, glycine buffer solution, borate buffer solution, or the like, is preferable. Concentration of buffering agent of the buffer solution is usually selected appropriately from a range of 10 to 500 mM, and preferably 10 to 100 mM. Concentration of the salt is usually 100 to 200 mM as concentration in the buffer solution.

As the surfactant for solubilizing the cells, any one usually used in this field may be used, and it may be selected appropriately according to conditions, such as the type of cells to be used, pH, and salt concentration of the buffer solution to be used. For example, NP-40, poly (oxyethylene) nonylphenyl ether (produced by Wako Pure Chemical Industries, Ltd.), Triton X-100, digitonin, or the like, is included, and, poly (oxyethylene) nonylphenyl ether is preferable. Concentration thereof may be such concentration that does not affect the nucleic acid-binding protein, and has cell lysis effect, and is preferably 0.01 to 1.0% relative to the total amount of the buffer solution.

In addition, a protease inhibitor and a phosphatase inhibitor are usually contained in the solution of the nucleic acid-binding protein or the cell lysate, to prevent the nucleic acid-binding protein from being decomposed.

When a cell culture supernatant or body fluid is used, a surfactant may be added as a solubilizing agent for cell secretory granules (exosomes). Examples of the surfactant to be used for this purpose include, for example, poly (oxyethylene) nonylphenyl ether (produced by Wako Pure Chemical Industries, Ltd.), Triton X-100, and the like, and poly(oxyethylene)nonylphenyl ether is preferable. Concentration thereof to be added is not especially limited, as long as it is such concentration that does not affect a nucleic acid-binding protein pertaining to the present invention, and has cell lysis effect, and is usually 0.01 to 0.5%, and preferably 0.05 to 0.1%, relative to the total amount of the sample.

A preferable aspect, a specific example, concentration, or the like, of each component to be used in the step B-1 such as the biotinylated nucleic acid and the solution containing the same, the tamavidin-immobilized insoluble carrier and the solution containing the same is the same as the one described in each of corresponding items and explanation on the step A-1 of the method for separating the biotinylated nucleic acid of the present invention.

In the step B-1, the method for contacting the sample containing the nucleic acid-binding protein, the biotinylated nucleic acid, and the tamavidin-immobilized insoluble carrier is selected appropriately depending on the type of the target nucleic acid-binding protein, or the type of the insoluble carrier to be used, and it may be any method where the complex of the nucleic acid-binding protein in the sample, the biotinylated nucleic acid, and the tamavidin-immobilized insoluble carrier is finally obtainable.

In the step B-1, when the sample containing the nucleic acid-binding protein, the biotinylated nucleic acid, and the tamavidin-immobilized insoluble carrier are contacted and reacted, concentration of the biotinylated nucleic acid in the reaction solution is usually 10 to 50 pmol, and preferably 10 to 20 pmol, relative to 0.1 to 1 mL of the sample.

In the step B-1, when the sample containing the nucleic acid-binding protein, the biotinylated nucleic acid, and the tamavidin-immobilized insoluble carrier are contacted and reacted, concentration of tamavidin in the reaction solution varies depending on the concentration of the biotinylated nucleic acid in the sample, and is not especially limited, and, it is usually 0.001 mM to 0.2 mM.

In the step B-1, when the sample containing the nucleic acid-binding protein, the biotinylated nucleic acid, and the tamavidin-immobilized insoluble carrier are contacted and reacted, content of the tamavidin-immobilized insoluble carrier in the reaction solution varies depending on the type of the carrier used, and when the insoluble carrier is particles or fine particles, it is usually 0.001 to 10 mg, and preferably 0.005 to 5 mg, relative to 0.1 to 1 mL of the sample. When the insoluble carrier is magnetic beads particles, it is usually 0.05 to 10 mg, and preferably 0.1 to 1 mg.

In the step B-1, when the sample containing the nucleic acid-binding protein, the biotinylated nucleic acid, and the tamavidin-immobilized insoluble carrier are contacted and reacted, reaction temperature is not especially limited, as long as it is in a range not inhibiting/suppressing the reaction of forming [the complex of the nucleic acid-binding protein, the biotinylated nucleic acid, and the tamavidin-immobilized insoluble carrier], and not separating the complex formed, and, it is preferably 3 to 30° C. Reaction time is 0.1 to 24 hours, and preferably 1 to 5 hours. At the time of the reaction, stirring treatment may be carried out, as necessary. When the other components are contacted and reacted, the reaction temperature and the reaction time are selected appropriately according to each condition explained in the step A-1 of the method for separating the biotinylated nucleic acid of the present invention.

For example, when the sample containing the nucleic acid-binding protein, the biotinylated nucleic acid (or a solution containing the same), and the tamavidin-immobilized insoluble carrier (or a solution containing the same) are contacted and reacted, pH of the reaction solution is not especially limited, as long as it is in a range not inhibiting/suppressing the reaction of forming the complex of the nucleic acid-binding protein, the biotinylated nucleic acid, and the tamavidin-immobilized insoluble carrier, and a range of pH 4.0 to 8.0, and preferably pH 7.0 to 7.5 is included.

In the step B-1, a specific method for making each component contacted and subjected to a reaction, includes, for example, the following methods, when the tamavidin-immobilized insoluble carrier is particles or fine particles:

(1) A method for mixing the sample containing the nucleic acid-binding protein with the solution containing the biotinylated nucleic acid, and then mixing with the tamavidin-immobilized insoluble carrier or the tamavidin-immobilized insoluble carrier solution.

(2) A method for mixing the sample containing the nucleic acid-binding protein with the tamavidin-immobilized insoluble carrier or the tamavidin-immobilized insoluble carrier solution, and then mixing with the solution containing the biotinylated nucleic acid.

(3) A method for mixing the sample containing the nucleic acid-binding protein with a reagent (reagent solution) containing [the complex of the tamavidin-immobilized insoluble carrier and the biotinylated nucleic acid].

When the insoluble carrier is a chip, a plate, or the like, the sample containing the nucleic acid-binding protein, the tamavidin-immobilized insoluble carrier (or a solution containing the same), and the biotinylated nucleic acid (or a solution containing the same) may be brought into contact.

After the reaction in step B-1, it is preferable to separate [the complex of the nucleic acid-binding protein, the biotinylated nucleic acid, and the tamavidin-immobilized insoluble carrier] from the obtained reaction solution. In addition, it is preferable to subject the obtained insoluble carrier to washing process with an appropriate washing solution, to remove foreign substances adhered to the insoluble carrier of the complex. The specific method, or the like, may be the similar method as separation/washing treatment which is preferably carried out before proceeding from the step A-1 to the step A-2.

(Step B-2)

Step B-2 of the method of the present invention for separating the biotinylated nucleic acid to which the nucleic acid-binding protein is bound is "a step for separating the biotinylated nucleic acid to which the nucleic acid-binding protein is bound from the complex obtained in the step B-1, in a solution having pH of 7.8 to 9.5, and in the presence of free biotin".

In step B-2, the [the complex of the nucleic acid-binding protein, the biotinylated nucleic acid, and the tamavidin-immobilized insoluble carrier] obtained in the step B-1 and free biotin are contacted and reacted in a solution of pH 7.8 to pH 9.5.

The method may be any method, as long as the solution of pH 7.8 to 9.5 containing the complex and the free biotin can be obtained.

In this step, the specific method, and preferable aspects of each constituent feature, specific examples and concentration, and the like, of the solution containing [the complex of the nucleic acid-binding protein, the biotinylated nucleic acid, and tamavidin-immobilized insoluble carrier], a solution containing free biotin, and a solution which makes pH of the solution after mixing in 7.8 to 9.5, or the like, and the reaction condition are the same as those described in the above explanation concerning the step A-2 of the method for separating the biotinylated nucleic acid of the present invention.

For example, the specific method includes the following methods, similarly as in the step A-2.

(1) A method for mixing [the complex of the nucleic acid-binding protein, the biotinylated nucleic acid, and the tamavidin-immobilized insoluble carrier] or the solution containing the complex with the solution containing free biotin, and then mixing with a solution which makes pH of the solution after mixing in 7.8 to 9.5, (2) a method for mixing the complex or the solution containing the complex with a solution which makes pH of the solution after mixing in 7.8 to 9.5, and then mixing with the solution containing free biotin, (3) a method for mixing the complex or the solution containing the complex with a solution which contains free biotin and makes pH of the solution after mixing in 7.8 to 9.5.

Among the methods (1) to (3), the method (3) is the most convenient and simple in consideration of work efficiency, or the like.

In particular, a method according to (3) and the method comprising removing the solvent from the solution containing [the complex of the nucleic acid-binding protein, the biotinylated nucleic acid, and the tamavidin-immobilized insoluble carrier] obtained in the step B-1 by a method depending on the property of the insoluble carrier, and then mixing the complex with a solution which contains free biotin and makes pH of the solution after mixing in 7.8 to 9.5 is simple and easy.

In this case, the solution to be used may be a solution having pH of 7.8 to 9.5, because after the solvent is removed, the complex is mixed with a solution which makes pH of the solution after mixing in 7.8 to 9.5.

The solvent to be used for the solution containing [the complex of the nucleic acid-binding protein, the biotinylated nucleic acid, and the tamavidin-immobilized insoluble carrier] pertaining to the step B-2, includes, for example, the same one as the solvent for suspending the tamavidin-immobilized insoluble carrier described in the step A-1, and it is not especially limited.

In the step B-2, the solvent to be used for preparing the solution containing free biotin includes, for example, potassium phosphate buffer solution, Tris buffer solution, phosphate buffered saline (PBS), HEPES buffer solution, borate buffer solution, phosphate buffer solution, veronal buffer solution, Good's buffer solution, or the like. In addition, concentration of the buffering agent of the buffer solution is selected appropriately from a range of usually 10 to 1000 mM, and preferably 10 to 100 mM.

Concentration of free biotin in the solution containing free biotin may be such concentration to be excess quantity, so that the complex can be separated into the biotinylated nucleic acid to which the nucleic acid-binding protein is bound and the tamavidin-immobilized insoluble carrier at pH 7.8 to 9.5, when mixed with [the complex of the nucleic acid-binding protein, the biotinylated nucleic acid, and the tamavidin-immobilized insoluble carrier], or when mixed with the solution containing the complex. Specifically, it is such concentration that provides 40 to 4000 times mol relative to the tamavidin supported on the insoluble carrier of the complex in the mixed solution, for example, such concentration that provides 2 to 40 mM relative to 0.01 to 0.05 mM tamavidin supported on the insoluble carrier of the complex in a mixed solution, when mixed with [the complex of the nucleic acid-binding protein, the biotinylated nucleic acid, and the tamavidin-immobilized insoluble carrier], or when mixed with the solution containing the complex.

The solution containing free biotin may further contain a sensitizer, a surfactant, a preservative (for example, sodium azide, salicylic acid, benzoic acid, or the like.), a stabilizer (for example, albumin, globulin, water-soluble gelatin, a surfactant, saccharides, or the like.), an activator, an effect avoiding agent of coexisting substances, or the like, and others which are usually used in this field. In addition, a concentration range, or the like, of these reagents, or the like, may be selected and used appropriately from a usually used range in the measurement method known per se.

A solution to be used in the step B-2 which makes pH of the solution after mixing of 7.8 to 9.5, includes, for example, buffer solution having buffering action at near pH 7.8 to pH 9.5, and specifically includes, for example, potassium phosphate buffer solution, Tris buffer solution, phosphate buffer solution, veronal buffer solution, Good's buffer solution, phosphate buffered saline (PBS), HEPES buffer solution, borate buffer solution, or the like. In addition, concentration of the buffering agent of these buffer solutions is selected appropriately from a range of usually 10 to 1000 mM, and preferably 10 to 100 mM.

In the case of using [the complex of the nucleic acid-binding protein, the biotinylated nucleic acid, and the tamavidin-immobilized insoluble carrier] which is not in a solution state in step B-2, for example, in the case where the step B-2 is the method (3) of mixing the complex with a solution which contains free biotin and makes pH of the solution after mixing in 7.8 to 9.5, a buffer solution having buffering action at near pH 7.8 to 9.5 may be used as a solution which makes pH of the solution after mixing in 7.8 to 9.5.

Concentration of free biotin in the reaction solution at the time of making the complex contacted and subjected to a reaction with free biotin at pH 7.8 to pH 9.5 in step B-2, is such a concentration of about 40 to 4000 times mol relative to concentration of tamavidin in the reaction solution, that is, relative to the tamavidin supported on the insoluble carrier in the reaction solution, because too high concentration will be waste of biotin. In addition, pH of the reaction solution is 7.8 to 9.5.

Reaction temperature, at the time of making the complex contacted and subjected to a reaction with free biotin at pH 7.8 to pH 9.5, in step B-2, includes usually a range of 3 to 50° C., and preferably 3 to 25° C. In addition, reaction time thereof is for about 1 to 360 minutes, preferably for about 10 to 180 minutes, and more preferably for about 10 to 30 minutes, in response to each reaction condition, because it varies depending on the reaction conditions such as the type of the biotinylated nucleic acid to be used, the type of the tamavidin-immobilized insoluble carrier, pH and temperature. During the reaction, mixing treatment may be carried out, as necessary.

When the biotinylated nucleic acid to be used is either the RNA or the DNA, pH in the step B-2 is preferably pH 7.8 to 9.5, more preferably pH 8.0 to 9.0, further more preferably pH 8.2 to 8.8. The pH of around 8.5 is particularly preferable.

By carrying out the step B-2, [the complex of the nucleic acid-binding protein, the biotinylated nucleic acid, and the tamavidin-immobilized insoluble carrier] is reacted with 40 to 4000 times mol of free biotin relative to the tamavidin, in the solution having pH of 7.8 to 9.5, and then the biotinylated nucleic acid to which the nucleic acid-binding protein is bound is separated from the complex.

Subsequently, the solution containing the biotinylated nucleic acid can be obtained, by separating the biotinylated nucleic acid to which the nucleic acid-binding protein is bound, and the tamavidin-immobilized insoluble carrier. A specific example of the method is similar to a method described in the invention relating to the step A-2.

The solution containing the biotinylated nucleic acid to which the nucleic acid-binding protein is bound can be easily obtained, by separating the biotinylated nucleic acid to which the nucleic acid-binding protein is bound and the tamavidin-immobilized insoluble carrier, which are present separately in the solution, for example, by a usual method depending on the type of the insoluble carrier used. For example, when the magnetic beads are used as the insoluble carrier, the solution containing the biotinylated nucleic acid to which the nucleic acid-binding protein is bound can be obtained by separating the tamavidin-immobilized magnetic beads by magnetic separation.

The solution containing the biotinylated nucleic acid may be recovered plural times, by carrying out several times of separation step of the biotinylated nucleic acid to which the nucleic acid-binding protein is bound remaining on the tamavidin-immobilized insoluble carrier, by adding the solution containing free biotin and the solution which makes pH of the solution after mixing in 7.8 to 9.5 to the tamavidin-immobilized insoluble carrier or the solution thereof after separation of the biotinylated nucleic acid to which the nucleic acid-binding protein is bound and the tamavidin-immobilized insoluble carrier, or by adding the solution which contains free biotin and makes pH of the solution after mixing in 7.8 to 9.5 to the tamavidin-immobilized insoluble carrier or the solution thereof after separation of the biotinylated nucleic acid to which the nucleic acid-binding protein is bound, and the tamavidin-immobilized insoluble carrier.

If necessary, the biotinylated nucleic acid may also be recovered from the solution containing the biotinylated nucleic acid to which the nucleic acid-binding protein is bound obtained in the step B-2, by further purification of the nucleic acid by a known nucleic acid extraction method, or the like. For example, a method for phenol/chloroform extraction, or a method using commercially available nucleic acid purification kit, or the like, is included.

It has become possible to recover the biotinylated nucleic acid to which the nucleic acid-binding protein is bound, in good yield by carrying out the method of the present invention for separating the biotinylated nucleic acid to which the nucleic acid-binding protein is bound.

In the method of the present invention for separating the biotinylated nucleic acid to which the nucleic acid-binding protein is bound, for example, the nucleic acid corresponding to the target nucleic acid-binding protein can be used as the nucleic acid to be used for the biotinylated nucleic acid. That is, for a known nucleic acid-binding protein, the corresponding nucleic acid capable of binding to the nucleic acid-binding protein may be used. In addition, when the method of the present invention for separating the biotinylated nucleic acid to which the nucleic acid-binding protein is bound is carried out using the nucleic acid whose corresponding binding protein is unknown, the unknown protein capable of binding to the used nucleic acid can be obtained.

The method of the present invention for separating the biotinylated nucleic acid to which the nucleic acid-binding protein is bound is explained specifically, for example, as follows, by taking the case as an example where the step B-1 is the method (1) (the method for mixing the sample containing the nucleic acid-binding protein with the solution containing the biotinylated nucleic acid, and then mixing with the tamavidin-immobilized insoluble carrier or the tamavidin-immobilized insoluble carrier solution).

To a pellet of $1 \times 10^7$ cells which is expected to contain the nucleic acid-binding protein, 500 µL of cell lysing agent (25 mM Tris-HCl, pH 7.4, 150 mM KCl, 0.5 mM DTT, 0.5% cell solubilizing surfactant, a protease inhibitor, and a phosphatase inhibitor) was added, and the cell pellets were suspended to incubate on ice for 1 to 5 minutes. After that, the cell suspension was centrifuged at 20,000×G for 15 minutes, and the obtained supernatant was used as a cell lysate. A 0.1 to 1 mL of the cell lysate is mixed with the solution containing the biotinylated nucleic acid (10 to 50 pmol), and subjected to a reaction at 3 to 30° C. for 0.1 to 24 hours, and preferably 1 to 5 hours.

Separately, 0.05 mg to 10 mg of the tamavidin 2-REV-immobilized magnetic beads (supported amount of tamavidin is 0.5 µg to 2000 µg, 0.3 nM to 1.3 µM, relative to 1 mg of the magnetic beads) is added into a tube, and after washing process, the washing solution is removed. Next, the mixed solution of the cell lysate and the biotinylated nucleic acid prepared previously is added to the tube, and reacted usually at 3 to 50° C., preferably 3 to 25° C. for 0.1 to 24 hours, and preferably for about 1 to 5 hours under stirring, to form the complex of the nucleic acid-binding protein, the biotinylated nucleic acid, and the tamavidin 2-REV-immobilized magnetic beads. After the reaction, the magnetic beads and the solution are separated using a magnetic stand. After washing process of the beads several times, the washing solution is removed. Next, 10 to 20 µL of an elution buffer (50 mM Tris-HCl, pH 7.8 to 9.5, containing 2 to 20 mM biotin) is added to the tube, and reacted under stirring, usually at 3 to 50° C., preferably 3 to 25° C., for 1 to 360 minutes, preferably 10 to 180 minutes, and further preferably 10 to 30 minutes. After the reaction, the eluate containing the biotinylated nucleic acid to which the nucleic acid-binding protein is bound, is separated and recovered, by removing the tamavidin 2-REV-immobilized magnetic beads using a magnetic stand. It is possible to separate the biotinylated nucleic acid to which the nucleic acid-binding protein is bound by performing the above operation.

The method for separating the biotinylated nucleic acid to which the nucleic acid-binding protein is bound, relevant to the present invention, may be carried out manually of course, and it goes without saying that an automated analyzer may be used, since the method of the present invention can be applied to a measurement system using an automated analyzer. It should be noted that combinations of reagents are not especially limited, when carrying out the measurement manually or using the automated analyzer, and it may be carried out appropriately according to environment of the automated analyzer to be applied, other factors, and the like.

After the step B-2, the nucleic acid-binding protein can be analyzed in a state that the nucleic acid-binding protein is bound to the biotinylated nucleic acid. For example, after the solvent is exchanged with 1% to 2% trichloroacetic acid, digestion with trypsin, and then analysis by a mass spectrometer may be carried out. Alternatively, there is also included a method for performing analysis, by adding a denaturant such as a 1 to 10% SDS solution, 7 M guanidine hydrochloride, pH 2.3 glycine solution, and an 8 M urea solution, or an SDS sample buffer, and then performing SDS-PAGE.

[C. Method for Separating Nucleic Acid-Binding Protein of the Present Invention]

The method for separating the nucleic acid-binding protein of the present invention comprises the following steps: (1) a step for contacting a sample containing the nucleic acid-binding protein, the biotinylated nucleic acid wherein biotin is bound to the nucleic acid, and the tamavidin-immobilized insoluble carrier to form a complex of the nucleic acid-binding protein, the biotinylated nucleic acid, and the tamavidin-immobilized insoluble carrier (step C-1), (2) a step for separating the biotinylated nucleic acid to which the nucleic acid-binding protein is bound from the complex obtained in the step C-1, in a solution having pH of 7.8 to 9.5, and in the presence of free biotin (step C-2), (3) a step for separating the nucleic acid-binding protein from the biotinylated nucleic acid to which the nucleic acid-binding protein is bound obtained in the step C-2 (step C-3).

Specific method of the step C-1 and preferable embodiments of each constituent feature and reagents in the step are the same as those described in explanation of on the step B-1 in the "Method for separating biotinylated nucleic acid to which the nucleic acid-binding protein is bound". Specific method of step C-2 and preferable embodiments of each constituent feature and reagents in the step are the same as those described in explanation in the step B-2 of the "Method for separating biotinylated nucleic acid to which the nucleic acid-binding protein is bound".

In addition, to carry out separation and washing treatment for the obtained complex, each between step C-1 and step C-2, and step C-2 and the step C-3, is the same as described above.

Normally, it is not necessary to separate the nucleic acid-binding protein from the biotinylated nucleic acid to which the nucleic acid-binding protein is bound, to analyze the nucleic acid-binding protein of the [biotinylated nucleic acid to which the nucleic acid-binding protein is bound] obtained in the step C-2. For example, [the biotinylated nucleic acid to which the nucleic acid-binding protein is bound] is separated by usual SDS-PAGE, or the like. The nucleic acid-binding protein may be extracted by a usual method, by cutting out a gel fraction containing the objective nucleic acid-binding protein, if necessary, after the SDS-PAGE, because the nucleic acid-binding protein is separated from the nucleic acid by SDS.

In addition, the nucleic acid-binding protein may be separated, as necessary, from the [the biotinylated nucleic acid to which the nucleic acid-binding protein is bound] obtained in the step C-2.

The step C-3 is a step for separating the nucleic acid-binding protein from the biotinylated nucleic acid to which the nucleic acid-binding protein is bound obtained in the step C-2.

The specific method include, for example, a method for purification of a protein component from the solution containing [the biotinylated nucleic acid to which the nucleic acid-binding protein is bound], by using TCA/acetone precipitation, methanol/chloroform extraction, or the like, a method for separation using a protein denaturant such as 2 to 4% SDS solution, 7 M guanidine hydrochloride, and pH 2.3 glycine solution, a method for boiling-after the addition of the sample buffer solution for SDS-PAGE, or the like.

[D. A Kit for Separating Nucleic Acid of the Present Invention]

The kit for separating the nucleic acid of the present invention is used for carrying out the method of the present invention as described above, that is, the method for separating the biotinylated nucleic acid, the method for separating the biotinylated nucleic acid to which the nucleic acid-binding protein is bound, or the method for separating the nucleic acid-binding protein, and the kit comprising a reagent containing an insoluble carrier on which tamavidin is immobilized, and a reagent which makes pH of the solution after mixing in 7.8 to 9.5, as constituent reagents.

The kit may contain a reagent comprising free biotin, as a constituent reagent.

In addition, it is also possible to constitute "a kit for separating the nucleic acid-binding protein" which contains a reagent for separating the nucleic acid-binding protein from the biotinylated nucleic acid to which the nucleic acid-binding protein is bound, as a constituent reagent.

Preferable aspect, specific example, concentration, and the like, of each constituent feature are as described in the explanation concerning the method of the present invention as described above, that is, the method for separating the biotinylated nucleic acid, the method for separating the biotinylated nucleic acid to which the nucleic acid-binding protein is bound, or the method for separating the nucleic acid-binding protein.

For example, preferable aspect, specific example, concentration and the like of a reagent which makes pH of the solution after mixing in 7.8 to 9.5, a reagent containing free biotin, and a insoluble carrier on which tamavidin is immobilized, are as described in the explanation concerning the method of the present invention as described above, that is, the method for separating the biotinylated nucleic acid, the method for separating the biotinylated nucleic acid to which the nucleic acid-binding protein is bound, or the method for separating the nucleic acid-binding protein, and it will be explained afresh below.

A specific example of the reagents containing the insoluble carrier on which tamavidin is immobilized includes a reagent comprising the tamavidin-immobilized insoluble carrier, or the tamavidin-immobilized insoluble carrier solution. The specific example thereof is as described above.

For example, a reagent which makes pH of the solution after mixing in 7.8 to 9.5 includes a solution which makes pH of the solution after mixing in 7.8 to 9.5 as described above. For example, a buffer solution having buffering action at near pH 7.8 to pH 9.5 is included, and includes specifically, for example, a potassium phosphate buffer solution, a Tris buffer solution, a phosphate buffer solution, a veronal buffer solution, a Good's buffer solution, a phosphate buffered saline (PBS), an HEPES buffer solution, a borate buffer solution, or the like. In addition, concentration of the buffering agent of these buffer solutions is selected appropriately from a range of usually 10 to 1000 mM, and preferably 10 to 100 mM.

In addition, pH of such a solution which makes pH after mixing in 7.8 to 9.5 is preferably pH 7.8 to 9.5, more preferably pH 8.0 to 9.0, and further preferably pH 8.2 to 8.8. The pH of around 8.5 is particularly preferable.

The reagent containing free biotin includes a solution containing the free biotin. Concentration of free biotin in the solution containing free biotin is not especially limited. For example, it may be the solution containing free biotin at a concentration of 2 mM to 1 M. The solution containing the free biotin may be added, so as to make a concentration of 40 to 4000 times mol relative to the tamavidin supported on the insoluble carrier in the complex in the mixed solution, when the solution containing the free biotin is mixed with [the complex of biotinylated nucleic acid (to which the nucleic acid-binding protein is bound) and the tamavidin-immobilized insoluble carrier], or when mixed with the solution containing the complex.

The solvent to be used to prepare the solution containing free biotin includes, for example, potassium phosphate buffer solution, Tris buffer solution, phosphate buffered saline (PBS), HEPES buffer solution, borate buffer solution, phosphate buffer solution, veronal buffer solution, Good's buffer solution, or the like. In addition, concentration of the buffering agent of these buffer solutions is selected appropriately from a range of usually 10 to 1000 mM, and preferably 10 to 100 mM.

In addition, each constituent reagent may be those in a solution state such as a suspension in which each reagent is suspended in an appropriate buffer solution, or it may be frozen products obtained by freezing it, or freeze-dried products thereof. Specific examples of the buffering agents and the like to be used for this purpose, pH and concentration thereof are as described above.

In addition, to these reagents contained in the kit, the reagents usually used in this field, for example, protease inhibitors, buffering agents, surfactants, stabilizers, and others used in this field, may be contained. These reagents may be prepared as a separated reagent, and may be added and mixed at the time of use. Concentration, pH, or the like in that case may be set to condition usually used.

In addition, in the case where the kit is composed of plurality of reagent solutions, these reagents may be contained by being appropriately separated in any one of the reagent solutions, so as to provide objective concentration at the time of mixing each of the reagent solutions. Using concentration of the reagents which constitute these reagent solutions may be selected appropriately from a range commonly used in this field.

Furthermore, a manual etc. for use in the method for separating the biotinylated nucleic acid may be included in the kit of the present invention. The "manual" means the instruction manual, the package insert, or brochure (leaflet), etc. of the kit, in which features, principles, operating procedures, and determination procedures, etc. of the method is described substantially in sentence or by figures, and tables.

Specific embodiments of the kit of the present invention include, for example, the following constitutions.
(1) The one having the first reagent comprising the tamavidin-immobilized insoluble carrier pertaining to the present invention, and the second reagent which makes pH of the solution after mixing in 7.8 to 9.5, as constituent reagents;
(2) The one having the first reagent comprising the tamavidin-immobilized insoluble carrier pertaining to the present invention, the second reagent which makes pH of the solution after mixing in 7.8 to 9.5, and the third reagent comprising free biotin, as constituent reagents;
(3) The one having the first reagent comprising the tamavidin-immobilized insoluble carrier pertaining to the present invention, and the second reagent which contains free biotin and makes pH of the solution after mixing in 7.8 to 9.5, as constituent reagents.

Hereinafter, the present invention will be explained more specifically in reference to EXAMPLES, however, the present invention should not be limited in any way by these EXAMPLES.

EXAMPLES

Example 1. Verification of Relationship Between Separation of Biotinylated RNA from Tamavidin 2-REV-Immobilized Insoluble Carrier and pH Dissociation efficiency of the biotinylated RNA from the tamavidin 2-REV-immobilized insoluble carrier was compared using various elution buffer solutions by the following method.
(1) Preparation of Tamavidin 2-REV-Immobilized Magnetic Beads To 1 mg of Dynabeads™ MyOne™ Carboxylic Acid (magnetic beads, particle size 2.7 µm, produced by Thermo Fisher Scientific Co., Ltd.), 50 µg of tamavidin 2™-REV (produced by Wako Pure Chemical Industries, Ltd.) was immobilized according to a protocol attached to Dynabeads™ MyOne™ Carboxylic Acid to obtain the tamavidin 2-REV-immobilized magnetic beads.

A solution of the tamavidin 2-REV-immobilized magnetic beads having a final beads concentration of 10 mg/mL was prepared (the supported amount of tamavidin 2-REV was 50 µg at maximum relative to 1 mg of the magnetic beads, tamavidin 2-REV supported amount of 10 mg/mL magnetic beads was 0.03 mM at maximum).
(2) Preparation of Biotinylated RNA
1) Synthesis of Biotinylated 7SK snRNA and Biotinylated HOTAIR RNA
<Cloning of Gene Sequence Used for Biotinylated RNA Synthesis, and Preparation of Template DNA to be Used for In Vitro Transcription>

Synthesis of DNA (SEQ ID NO: 2) having a gene sequence encoding a human-derived 7SK snRNA, and DNA (SEQ ID NO: 3) having a gene sequence encoding a human-derived HOTAIR RNA, which are artificial genes, and cloning of the synthesized DNA in between cleavage sites of the EcoRI and SpeI of a pGEM-T Easy vector (The vector has T7 and SP6 which are recognition sites of RNA polymerase promoters on both sides of the multiple cloning sites, produced by Promega Corporation) were obtained by ordering to FASMAC Co., Ltd.

PCR amplification was carried out, using each of the obtained recombinant vectors as a template, and using a T7 primer and an Sp6 primer (both primers are universal primers, produced by Takara Bio Inc.).
Subsequently, after carrying out usual agarose gel electrophoresis for the obtained PCR amplification product, the PCR amplified fragments containing the gene sequence of the human-derived 7SK snRNA, and the PCR amplified fragments containing the gene sequence of the human-derived HOTAIR RNA were obtained, by carrying out gel extraction and purification, using QIAquick™ Gel Extraction Kit (Qiagen Inc.).
<Synthesis of Biotinylated RNA by In Vitro Transcription>

The biotinylated RNA was obtained by carrying out RNA synthesis by in vitro transcription, using each of the PCR amplified fragments obtained above as a template, and using a MEGAscript™ T7 Transcription Kit (produced by Ambion Inc., and sold by Thermo Fisher Scientific Co., Ltd.), according to a protocol attached to the kit. On this occasion, Biotin-16-UTP (produced by Roche Diagnostics Co., Ltd.) was used as a biotinylation substrate, and for the other substrates, the substrates attached to the Kit were used. UTP and Biotin-16-UTP were used in a molar ratio of 3:1.

Purification of the obtained biotinylated RNA (biotinylated 7SK snRNA and biotinylated HOTAIR RNA) was carried out, using a PureLink™ RNA Mini Kit (produced by Ambion Inc., sold by Thermo Fisher Scientific Co., Ltd.).
2) Synthesis of 3' Terminal Biotinylated RNA Oligo (3'-Biotin Mir-92a RNA Oligo)

Synthesis of an RNA oligo (3'-Biotin mir-92a RNA oligo), of which 3' terminal of mir-92a (SEQ ID NO: 4), which is a human-derived microRNA, is biotinylated, was obtained by ordering to Nippon Gene Materials Co., Ltd. The obtained 3'-Biotin mir-92a RNA oligo was adjusted to 1 µg/µL, using RNase-free water.
(3) Separation/Recovery Test of Biotinylated RNA Three types of the biotinylated RNA (biotinylated 7SK snRNA, biotinylated HOTAIR RNA, 3'-Biotin mir-92a RNA oligo) prepared in the (2) were each diluted using PBS, so as to attain 20 ng/µL. Concentration of the RNA in each biotinylated RNA solution was calculated by measuring absorbance at 260 nm.

Separately, each 0.1 mg of the tamavidin 2-REV-immobilized magnetic beads (beads concentration is 10 mg/mL, amount of tamavidin 2-REV is 0.03 mM at maximum)

prepared in the (1) was added to nine 1.5 mL tubes. Next, 1 mL of PBS was added to each tube, thoroughly stirred using a vortex mixer, and then the magnetic beads and the solution were separated using a dedicated magnetic stand. The separated PBS solution was carefully discarded using a pipette (washing process of the magnetic beads).

To the magnetic beads after washing process, each 50 µL of previously prepared 20 ng/µL of various types of biotinylated RNA solutions (biotinylated 7SK snRNA, biotinylated HOTAIR RNA, 3'-Biotin mir-92a RNA oligo) was added into three tubes. Thereafter, each tube was subjected to a reaction at room temperature for 1 hour, under stirring using a tube mixer.

After the reaction, the magnetic beads and the solution were separated using a magnetic stand. After discarding the supernatant using a pipette, 1 mL of a washing buffer solution (20 mM Tris-HCl, pH 7.4, containing 200 mM NaCl, 2.5 mM $MgCl_2$, 0.05% NP-40) was added to each tube, to wash the magnetic beads three times. After the washing process, the washing buffer solution was discarded.

Next, each 20 µL of 20 mM Biotin/50 mM Potassium phosphate, pH 7.0 (it may be abbreviated as 50 mM KPB in some cases), 20 mM Biotin/50 mM Tris-HCl, pH 8.0, or 20 mM Biotin/50 mM Tris-HCl, pH 9.0, was added to each tube as an elution buffer solution, and subjected to a reaction under stirring, using a tube mixer at room temperature for 15 minutes. Molar concentration of tamavidin 2-REV in the reaction solution during the reaction was about 0.016 nmol/µL.

After the reaction, the eluate was separated using a magnetic stand, and the separated eluate was transferred to a new tube. This elution step was repeated once again, and the obtained eluate was pooled in the previously dispensed tube to collect in one tube. The beads after elution treatment were preserved.

RNA concentration of the obtained eluate was calculated by measuring absorbance at 260 nm. Based on the obtained concentration of RNA, the ratio (recovery efficiency, %) of the RNA concentration in the obtained eluate, relative to the RNA concentration in each of the biotinylated RNA solutions used, was determined to compare RNA recovery performance.

(4) Results

The results are shown in FIG. 1. In FIG. 1, each column represents results when the following biotinylated RNAs were separated: 3'-Biotin mir-92a RNA oligo (clear column), Biotinylated 7SK snRNA (striped column), and Biotinylated HOTAIR RNA (black column).

As is clear from FIG. 1, in all cases where various biotinylated RNAs were separated, recovery efficiency of the biotinylated RNA was higher in the case of separation using 20 mM Biotin/50 mM Tris-HCl, pH 8.0, and the case of separation using 20 mM Biotin/50 mM Tris-HCl, pH 9.0, as compared with the case of separation using 20 mM Biotin/50 mM KPB, pH 7.0, which is a neutral range elution buffer. Particularly, in the case of the biotinylated HOTAIR RNA, biotinylated HOTAIR RNA could be recovered by only about 60% when the separation was carried out using the 20 mM Biotin/50 mM KPB solution, pH 7.0, whereas it has been revealed that nearly 100% of the biotinylated HOTAIR RNA could be recovered when the separation was carried out using 20 mM Biotin/50 mM Tris-HCl, pH 9.0.

Example 2. Dissociation of Biotinylated DNA from Tamavidin 2-REV-Immobilized Insoluble Carrier Dissociation efficiency of the biotinylated DNA from the tamavidin 2-REV carrier was compared using various elution buffer solutions, by the following method.

(1) Synthesis of Biotinylated ssDNA (Single-Stranded DNA) and Biotinylated dsDNA (Double-Stranded DNA)

1) Synthesis of Biotinylated 7SK ssDNA

Into a reaction tube, 1 µg of a PCR amplified fragment containing a gene sequence of the human-derived 7SK snRNA obtained in Example 1 (2) 1) was added, and as a substrate, 0.2 mM dATP, 0.2 mM dCTP, 0.2 mM dGTP, 0.15 mM dTTP, and 0.05 mM Biotin-11-dUTP (all are the final concentrations at the time of reaction. dATP, dCTP, dGTP, dTTP are produced by Wako Pure Chemical Industries, Ltd., and dBiotin-11-dUTP is produced by Thermo Fisher Scientific Co., Ltd.) using TaKaRa Ex Taq™ Hot Start Version (produced by Takara Bio Inc.) were added. The dTTP and Biotin-11-dUTP were added in a ratio of 3:1.

Subsequently, a 100 µM T7 primer was added to the reaction tube so as to attain the final concentration of 0.5 µM, and the PCR reaction was carried out under the condition that after heat denaturation at 94° C. for 3 minutes, a cycle reaction at 98° C. for 10 seconds, at 57° C. for 30 seconds, and at 72° C. for 30 seconds was carried out 40 times to obtain a PCR extension sample.

The obtained PCR extension sample was purified using a QIAquick™ PCR Purification Kit (produced by Qiagen Inc.) to obtain the biotinylated 7SK ssDNA. Concentration of the obtained biotinylated 7SK ssDNA was measured and calculated using NanoDrop 1000 (produced by Thermo Fisher Scientific Co., Ltd.).

2) Synthesis of Biotinylated 7SK dsDNA

The biotinylated 7SK dsDNA was synthesized by carrying out the same reaction using the same reagent as in the "1) Synthesis of biotinylated 7SK ssDNA", except for using the T7 primer and an SP6 primer each having the final concentration of 100 µM, as primers.

The obtained PCR amplified sample was purified using the QIAquick™ PCR Purification Kit (produced by Qiagen Inc.) to obtain the biotinylated 7SK dsDNA. Concentration of the obtained biotinylated 7SK dsDNA was measured and calculated using NanoDrop 1000 (manufactured by Thermo Fisher Scientific Co., Ltd.).

(2) Recovery Test of Biotinylated DNA

The biotinylated 7SK ssDNA and the biotinylated dsDNA, both prepared in the (1), were each diluted to 20 ng/µL using PBS. RNA concentration of each biotinylated RNA solution was calculated by measuring absorbance at 260 nm.

Separately, each 0.1 mg of the tamavidin 2-REV-immobilized magnetic beads (beads concentration is 10 mg/mL, tamavidin 2-REV amount is 0.03 mM at maximum) prepared in Example 1 was added to six 1.5 mL tubes. Next, 1 mL of PBS was added to each tube, and after thoroughly stirring using a vortex mixer, the magnetic beads and the solution were separated using a dedicated magnetic stand. The separated PBS solution was carefully discarded using a pipette (washing treatment of magnetic beads).

To the magnetic beads after washing treatment, each 25 µL of previously prepared 20 ng/µL of various types of the biotinylated DNA solutions (biotinylated 7SK ssDNA, biotinylated dsDNA) was added to three tubes. Thereafter, each tube was subjected to a reaction at room temperature for 1 hour, under stirring using a tube mixer, or the like.

After the reaction, the magnetic beads and the solution were separated using a magnetic stand. After discarding the supernatant using a pipette, 1 mL of a washing buffer solution (20 mM Tris-HCl, pH 7.4, 200 mM NaCl, 2.5 mM $MgCl_2$, 0.05% NP-40) was added to each tube, and the magnetic beads were subjected to washing treatment three times. After washing treatment, the washing buffer solution was discarded.

Next, each 15 μL of 20 mM Biotin/50 mM KPB, 20 mM Biotin/50 mM Tris-HCl, pH 8.0, or 20 mM Biotin/50 mM Tris-HCl, pH 9.0, was added to each tube as an elution buffer, and subjected to a reaction at room temperature for 15 minutes, under stirring using a tube mixer. Molar concentration of tamavidin 2-REV in the reaction solution during the reaction was about 0.021 nmol/μL.

After the reaction, the eluate was separated using a magnetic stand, and the separated eluate was transferred to a new tube. This elution step was repeated once again, and the obtained eluate was pooled in the previously dispensed tube to collect in one tube. The beads after elution treatment were preserved.

DNA concentration of the obtained eluate was calculated by measuring absorbance at 260 nm. Based on the obtained DNA concentration, the ratio (recovery efficiency, %) of DNA concentration of the obtained eluate, relative to DNA concentration of each biotinylated DNA solution used, was determined to compare DNA recovery performance.

(4) Results

The results are shown in FIG. 2 (1) and FIG. 2 (2). FIG. 2 (1) shows the results on recovery efficiency of the biotinylated 7SK ssDNA, and FIG. 2 (2) shows the results on recovery efficiency of the biotinylated 7SK dsDNA.

As is clear from FIG. 2 (1) and FIG. 2 (2), both in the case of the biotinylated 7SK ssDNA (FIG. 2 (1)), and in the case of the biotinylated 7SK dsDNA (FIG. 2 (2)), recovery efficiency was higher in the case of separation using 20 mM Biotin/50 mM Tris-HCl, pH 8.0, and the case of separation using 20 mM Biotin/50 mM Tris-HCl, pH 9.0, as compared with the case of separation using 20 mM Biotin/50 mM KPB which is a neutral range elution buffer.

From the above results, it has been revealed that dissociation of binding of the tamavidin 2-REV magnetic beads with the biotinylated single-stranded DNA, and binding of the tamavidin 2-REV magnetic beads with the biotinylated double-stranded DNA were enhanced, and thereby, the biotinylated single-stranded DNA (ssDNA) and the biotinylated double-stranded DNA (dsDNA) can be efficiently recovered, by increasing pH of the solution to pH 9.0 in the presence of excess quantity of free biotin.

Comparative Example 1. Influence of pH on Dissociation Efficiency of Binding Between Tamavidin 2-REV and Biotin Comparison of dissociation efficiency of tamavidin 2-REV from the biotin carrier not bound to the nucleic acid was carried out using various elution buffers, by the following method.

(1) Test on Biotin Dissociation Property of Tamavidin 2-REV

To a freeze-dried product of tamavidin 2-REV (produced by Wako Pure Chemical Industries, Ltd.), 1.67 mL of distilled water was added to prepare a tamavidin 2-REV solution having a concentration of 0.6 mg/mL.

Separately, 200 μL of biotin agarose beads (produced by Sigma-Aldrich Co. LLC.) to which biotin is immobilized, was dispensed into two 1.5 mL tubes. PBS 1 mL was added thereto, and stirred thoroughly using a vortex mixer, and then subjected to centrifugation treatment at 8,000×G for 5 minutes. After centrifugation treatment, the supernatant was removed using a pipette, and the same operation was repeated twice to equilibrate the biotin agarose beads. Next, 0.84 mL of the 0.6 mg/mL tamavidin 2-REV solution previously prepared was added to each tube, and the mixture was subjected to a reaction, at room temperature for 1.5 hour, under stirring using a rotator.

After that, the mixture was centrifuged at 8,000×G for 5 minutes, and the supernatant was recovered as a Flowthrough fraction from each tube. To the remaining beads, 0.5 mL of 20 mM Biotin/50 mM KPB, pH 7.0, or 20 mM Biotin/50 mM Tris-HCl, pH 9.0, was added as an elution buffer, and subjected to a reaction, at room temperature for 5 minutes, under stirring using a rotator. Concentration of tamavidin 2-REV in the reaction solution during the reaction was 0.6 mg/mL.

After the reaction, centrifugation was carried out at 8,000×G for 5 minutes, and the supernatant of each tube was recovered as an elution fraction (elution fraction 1) (elution step 1). The elution step was repeated four times, and the elution fraction for five fractions in total was obtained in the first to the fifth elution steps. Each of protein concentration was calculated by measuring absorbance (A 280) of the initially added tamavidin 2-REV solution (tamavidin 2-REV solution at concentration of 0.6 mg/mL), a Flowthrough fraction, and elution fractions 1 to 5 (converted using OD 280=0.68, at 0.25 mg/mL).

Based on the obtained protein concentration, ratio (recovery efficiency, %) of the protein concentration in the obtained eluate, relative to the protein concentration in the tamavidin 2-REV solution used was determined to compare recovery performance of tamavidin 2-REV.

(2) Results

The results are shown in FIG. 3. In FIG. 3, the column of □ shows the results of separation of tamavidin 2-REV and the biotinylated agarose beads using 20 mM Biotin/50 mM KPB, pH 7.0, and the column of ■ shows the results of separation of tamavidin 2-REV and the biotin-immobilized agarose beads using 20 mM Biotin/50 mM Tris-HCl pH, 9.0.

As is clear from FIG. 3, it has been revealed that the recovery rate of tamavidin 2-REV at the second elution reached 100%, when separation of tamavidin 2-REV and the biotinylated agarose beads was carried out using 20 mM Biotin/50 mM KPB, pH 7.0 as an elution buffer, whereas recovery rate of tamavidin 2-REV reached 100% at the fourth time of elution, when separation of tamavidin 2-REV and the biotinylated agarose beads was carried out using 20 mM Biotin/50 mM Tris-HCl, pH 9.0 as an elution buffer.

As is clear from the above results, it has not been confirmed any change in dissociation of binding of tamavidin 2-REV and biotin, even when pH of the elution buffer containing excess quantity of free biotin was shifted to an alkaline side. That is, unlike the results of Example 1 and Example 2, such the phenomenon that dissociation can be enhanced in binding between biotin not bound to the nucleic acid and tamavidin was not confirmed, even by increasing pH of the solution in the presence of excess quantity of free biotin.

Consequently, it has been suggested that, phenomenon that dissociation of biotin and tamavidin 2-REV is enhanced by raising pH in the presence of excess quantity of free biotin is generated in binding between the biotinylated nucleic acid and tamavidin 2-REV, and therefore, this phenomenon is generated by a mechanism different from phenomenon that binding between biotin not bound to nucleic acid and tamavidin dissociates in the presence of excess quantity of free biotin.

Example 3. Study on pH Range Effective for Dissociation of Biotinylated Nucleic Acid from Tamavidin 2-REV-Immobilized Insoluble Carrier The effective pH range was verified by carrying out comparison of dissociation efficiency of biotinylated RNA from the tamavidin 2-REV-immobilized insoluble carrier using various elution buffers with different pH, by the following method.

(1) Separation/Recovery Test of Biotinylated RNA

The biotinylated HOTAIR RNA prepared in Example 1 was diluted to 40 ng/μL using PBS, and RNA concentration of the biotinylated HOTAIR RNA solution was calculated by measuring absorbance at 260 nm.

Separately, each 0.2 mg of the tamavidin 2-REV-immobilized magnetic beads (beads concentration is 10 mg/mL, tamavidin 2-REV amount is 0.03 mM at maximum), prepared in Example 1, was added to six 1.5 mL tubes. Next, 1 mL of PBS was added to each tube, and after thoroughly stirring using a vortex mixer, the magnetic beads and the solution were separated using a dedicated magnetic stand. The separated PBS solution was carefully discarded using a pipette (washing treatment of magnetic beads).

To the magnetic beads after washing treatment, each 50 μL of the previously prepared 40 ng/μL biotinylated HOTAIR RNA solution was added to each tube. Thereafter, each tube was subjected to a reaction at 4° C. for 4 hours, under stirring using a tube mixer, or the like.

After the reaction, the magnetic beads and the solution were separated using a magnetic stand. After discarding the supernatant using a pipette, 0.5 mL of a washing buffer (20 mM Tris-HCl, pH 7.4, 200 mM NaCl, 2.5 mM $MgCl_2$, 0.05% NP-40) was added to each tube, and washing treatment of the magnetic beads was carried out three times. After washing treatment, the washing buffer was discarded.

Next, each 20 μL of eight kinds of elution buffers having different pH (8 mM Biotin/50 mM Tris-HCl, pH 7.4, pH 7.6, pH 7.8, pH 8.0, pH 8.2, pH 8.5, pH 9.0, and pH 9.5), or as a control, eight kinds of buffer solutions having different pH which is the base of the elution buffer (buffer solutions not containing excess quantity of free biotin), was added to each tube and subjected to a reaction at 4° C. for 15 minutes, under stirring using a tube mixer. Molar concentration of tamavidin 2-REV in the reaction solution during the reaction was about 0.032 nmol/μL.

After the reaction, the eluate was separated using a magnetic stand, and the separated eluate was transferred to a new tube. This elution step was repeated once again, and the obtained eluate was pooled in the previously dispensed tube to collect in one tube. The beads after elution treatment were preserved.

RNA concentration of the obtained eluate was calculated by measuring absorbance at 260 nm. Subsequently, difference in RNA amount in the eluate was calculated from, RNA amount in the eluate when elution of the biotinylated HOTAIR RNA was carried out using an elution buffer containing excess quantity of free biotin, and RNA amount in the eluate when elution of the biotinylated HOTAIR RNA was carried out similarly using a buffer solution of the same pH without containing free biotin measured as a control. Based on the RNA concentration obtained by the above procedure, ratio (recovery efficiency, %) of RNA concentration of the obtained eluate, relative to RNA concentration in the biotinylated HOTAIR RNA solution used, was determined to carry out comparison of RNA recovery performance.

(2) Results

The results are shown in FIG. 4.

As is clear from FIG. 4, it has been confirmed in a range pH 7.8 to pH 9.5 that the elution efficiency of the biotinylated HOTAIR RNA tends to enhanced, whereas in a range of pH 7.4 to pH 7.6, the elution efficiency of that is almost flat. In addition, elution efficiencies were higher in the case of using an elution buffer in all a range of pH 7.8 to pH 9.5, as compared with the case of using the elution buffer in a range of pH 7.4 to 7.6.

From these results, it has been clarified that such synergic effect is observed that the recovery efficiency of the biotinylated nucleic acid bound to the tamavidin 2-REV-immobilized magnetic beads is increased by adding excess free biotin and increasing pH of the elution buffer to pH 7.8 or higher.

Example 4. Comparison of Elution Efficiency of RNA-Binding Protein from Tamavidin 2-REV Carrier in RNA Pull-Down Assay Comparison of elution efficiency of the RNA-binding protein from the tamavidin 2-REV-immobilized insoluble carrier in RNA pull-down assay was carried out using various elution buffers, by the following method.

(1) Preparation of Cell Lysate to be Used for RNA Pull-Down Assay

K562 cells (human chronic myelogenic leukemia cell, JCRB0019, RIKEN BioResource Center) were cultured in a 75 $cm^2$ flask using 20 mL of DMEM (produced by Wako Pure Chemical Industries, Ltd.) containing 10% FBS at 37° C. under 5% $CO_2$ atmosphere, up to 70% to 90% confluence. After culturing, the culture solution was transferred to a 50-mL centrifugal tube, and subjected to centrifugation operation at 400×G for 5 minutes. After centrifugation operation, the supernatant was removed, PBS was added to re-suspend the cells, and centrifuged again. After removal of the supernatant, the cells were re-suspended in appropriate amount of PBS, and cell number was counted. The cell suspension was dispensed into tubes to provide each $1 \times 10^7$ cells, and then subjected to centrifugation operation again, and the supernatant was removed to prepare cell pellets. To the obtained cell pellets, 500 μL of an RIP buffer (25 mM Tris-HCl, pH 7.4, containing 150 mM KCl, 0.5 mM DTT, 0.5% NP-40, a protease inhibitor (produced by Wako Pure Chemical Industries, Ltd.)), and a phosphatase inhibitor (produced by Wako Pure Chemical Industries, Ltd.) were added, and the cell pellets were suspended using a vortex mixer, and then incubated on ice for 5 minutes. After that, the cell suspension was centrifuged at 20,000×G for 15 minutes, and the obtained supernatant was used as a cell lysate for use in the RNA pull-down assay.

(2) RNA Pull-Down Assay

Into a 1.5 mL tube, 15 pmol amount of the biotinylated 7SK snRNA solution (in RNase free water) obtained in Example 1 was dispensed, and after heat treatment at 90° C. for 2 minutes, the tube was quenched immediately by placing it on ice for 2 minutes. Thereafter, 50 times volume of an RNA reconstitution buffer (10 mM Tris-HCl, pH 7.4, containing 0.1 M KCl and 10 mM $MgCl_2$) relative to the human-derived 7 SK snRNA solution was added, and subjected to a reaction at room temperature for 20 minutes. After the reaction, 500 μL of the cell lysate prepared in the (1) was added and subjected to a reaction at 4° C. for 4 hours, under stirring using a rotator.

Separately, each 50 μL of the tamavidin 2-REV-immobilized magnetic beads (beads concentration is 10 mg/mL, tamavidin 2-REV amount is 0.03 mM at maximum), prepared in Example 1, was added to three 1.5 mL tubes. Next, 1 mL of PBS was added to each tube, and after thoroughly stirring using a vortex mixer, the magnetic beads and the solution were separated using a magnetic stand. The separated PBS solution was discarded using a pipette (washing treatment of magnetic beads).

To the magnetic beads after the washing treatment, whole amount of the previously prepared reaction solution of the biotinylated 7SK snRNA and the cell lysate was added to each of the three tubes. Thereafter, each tube was subjected to a reaction at 4° C. for 1 hour, under stirring using a rotator.

After the reaction, the beads and the solution were separated using a magnetic stand. After discarding the supernatant using a pipette, a washing buffer (20 mM Tris-HCl, pH 7.4, containing 200 mM NaCl, 2.5 mM $MgCl_2$, 0.05% NP-40) was added to each tube, and the magnetic beads were subjected to washing treatment three times. After the washing treatment, the washing buffer was discarded.

Next, each 15 μL of 20 mM Biotin/50 mM KPB, pH 7.0, 20 mM Biotin/50 mM Tris-HCl, pH 8.0, or 20 mM Biotin/50 mM Tris-HCl, pH 9.0, was added to the tube as an elution buffer, and subjected to a reaction at room temperature for 15 minutes, under stirring using a tube mixer. Molar concentration of tamavidin 2-REV in the reaction solution during the reaction is about 0.1 nmol/μL.

After the reaction, the eluate was separated using a magnetic stand, and the separated eluate was transferred to a new tube. This elution step was repeated once again, and the obtained eluate was pooled in the previously dispensed tube to collect in one tube (it is referred to as "the RNA pull-down sample"). The beads after elution treatment were preserved.

(3) Western Blotting

1) Preparation of Sample for Western Blotting

Each of the whole amounts of the RNA pull-down sample obtained in the above (2) was mixed with 10 μL of 4× sample buffer solutions (produced by Wako Pure Chemical Industries, Ltd.) to obtain each 40 μL of the sample for western blotting.

In addition, in order to detect the protein remaining, on the surface of the beads even after the biotin elution treatment, each 40 μL of the sample for western blotting was obtained, by adding 40 μL of 2× sample buffer solutions (containing SDS, produced by Wako Pure Chemical Industries, Ltd.) to the beads after the elution treatment which is obtained in the above (2), and mixing, and then separating the solution using a magnetic stand after heating it at 98° C. for 5 minutes.

2) Western Blotting

Each 20 μL of the sample for western blotting obtained in the 1) was applied on a Super Sep Aces 5-20% gel (produced by Wako Pure Chemical Industries, Ltd.), and subjected to electrophoresis at 25 mA for 60 minutes. The obtained gel was transcribed on a PVDF membrane (produced by Millipore Corporation) at 1 $mA/cm^2$ for 60 minutes, using a semi-dry blotter and a discontinuous buffer (Anode buffer 1: 0.3 M Tris/5% Methanol, Anode buffer 2: 0.025 M Tris/5% Methanol, Cathode buffer: 0.025 M Tris/0.04 M aminocaproic acid/5% Methanol). To the transferred PVDF membrane, 3% skimmed milk diluted with PBS-T was added for a reaction at room temperature for 1 hour for blocking, and then 2 mL of an anti-human HEXIM 1 rabbit polyclonal antibody (produced by Abcam plc.) diluted 1000 times using PBS-T was added, and reacted at 4° C. for 16 hours. After washing three times using PBS-T, a secondary antibody [anti-rabbit IgG (H+L), mouse IgG fraction, peroxidase-conjugated antibody (produced by Wako Pure Chemical Industries, Ltd.)] diluted 10,000 times using PBS was subjected to a reaction at room temperature for 1 hour. The PVDF membrane after the reaction was washed five times using PBS-T, then immersed in a solution containing ImmunoStar Zeta (a chemiluminescent reagent, produced by Wako Pure Chemical Industries, Ltd.), and subjected to a reaction for 5 minutes. Then each of luminescent signal was detected using ImageQuant LAS-4000 (manufactured by GE Healthcare Japan Co., Ltd.).

(4) Results

Results obtained are shown in FIG. 5 (1) and FIG. 5 (2).

FIG. 5 (1) shows results of electrophoresis using the sample for western blotting eluted using each of three kinds of elution buffers after pull down. As is clear from FIG. 5 (1), it has been confirmed that more amount of HEXIM 1, which is the RNA-binding protein binding to the human-derived 7SK snRNA, was detected in the case where the elution was carried out using 20 mM Biotin/50 mM Tris-HCl, pH 8.0 as an elution buffer, and 20 mM Biotin/50 mM Tris-HCl, pH 9.0 as an elution buffer, as compared with the case where the elution was carried out using 20 mM Biotin/50 mM KPB, pH 7.0 as an elution buffer.

In addition, FIG. 5 (2) shows results of electrophoresis using the sample for western blotting obtained by SDS-denatured elution of the protein remaining on the surface of the beads after biotin elution treatment. As is clear from FIG. 5 (2), it has been confirmed that HEXIM 1 remaining on the beads was little detected under elution conditions of using 20 mM Biotin/50 mM Tris-HCl pH 8.0, and 20 mM Biotin/50 mM Tris-HCl, pH 9.0, whereas HEXIM 1 remained on the beads after elution with excessive biotin using 20 mM Biotin/50 mM KPB, pH 7.0.

From the above results, "the biotinylated 7SK snRNA to which HEXIM1 is bound" and "the tamavidin 2-REV immobilized magnetic beads" could be separated from the complex, by reacting the cell lysate of the K562 cell with the biotinylated 7SK snRNA to bind HEXIM1 in the cell lysate to the biotinylated 7SK snRNA, and then by reacting with the tamavidin 2-REV-immobilized magnetic beads to form "the complex of HEXIM1, the biotinylated 7SK snRNA, and the tamavidin 2-REV-immobilized magnetic beads", and then, by shifting pH of the solution containing the relevant complex to an alkaline side in the presence of excess quantity of free biotin. In addition, the tamavidin 2-REV-immobilized magnetic beads after separation were treated by SDS to examine amount of the remaining protein without being separated on the surface of the beads, and it has been confirmed that almost no protein remained on the beads. From the above results, it has been confirmed that the nucleic acid-binding protein can be separated in extremely high efficiency and high accuracy by the method of the present invention.

Furthermore, from the above results, it has been revealed that elution efficiency, also in the RNA pull-down assay in actual use, can be enhanced by using the elution buffer of a higher alkaline side, as compared with that in a neutral range.

INDUSTRIAL APPLICABILITY

According to the present invention, the biotinylated nucleic acid can be obtained efficiently and in good precision, by using the tamavidin-bound insoluble carrier relevant to the present invention, and by shifting pH of the solution to an alkaline side of 7.8 to 9.5 in the presence of excess quantity of free biotin.

In addition, according to the method of the present invention, the complex of the nucleic acid-binding protein and the biotinylated nucleic acid can be obtained efficiently and in high precision. In addition, the complex of the unknown nucleic acid-binding protein and the nucleic acid can be isolated, even in the case of the nucleic acid whose binding protein is unknown. From the above, the present invention is also useful for functional analysis of the non-coding nucleic acid, and for research on the nucleic acid-binding proteins.

The invention claimed is:

1. A method for separating a biotinylated nucleic acid, comprising the following steps:
   (1) a step for contacting a sample containing a biotinylated nucleic acid wherein the biotin is bound to the nucleic acid with an insoluble carrier on which tamavidin is immobilized (a tamavidin-immobilized insoluble carrier) to form a complex of the biotinylated nucleic acid and the tamavidin-immobilized insoluble carrier (step A-1),
   (2) a step for separating the biotinylated nucleic acid from the complex obtained in the step A-1, in a solution having pH of 7.8 to 9.5, and in the presence of free biotin (step A-2).

2. The method according to claim 1, wherein the tamavidin is tamavidin 2-REV.

3. The method according to claim 1, wherein the step A-1 is carried out in the presence of 40 to 4000 times mol of free biotin relative to the tamavidin.

4. A method for separating a biotinylated nucleic acid to which a nucleic acid-binding protein is bound, comprising the following steps:
   (1) a step for contacting a sample containing a protein capable of binding to a nucleic acid (a nucleic acid-binding protein), a biotinylated nucleic acid wherein the biotin is bound to the nucleic acid, and a tamavidin-immobilized insoluble carrier to form a complex of the nucleic acid-binding protein, the biotinylated nucleic acid, and the tamavidin-immobilized insoluble carrier (step B-1),
   (2) a step for separating the biotinylated nucleic acid to which the nucleic acid-binding protein is bound from the complex obtained in the step B-1, in a solution having pH of 7.8 to 9.5, and in the presence of free biotin (step B-2).

5. The method according to claim 4, wherein the tamavidin is tamavidin 2-REV.

6. The method according to claim 4, wherein the step B-1 is carried out in the presence of 40 to 4000 times mol of free biotin relative to the tamavidin.

7. A method for separating a nucleic acid-binding protein, comprising the following steps:
   (1) a step for contacting a sample containing a nucleic acid-binding protein, a biotinylated nucleic acid wherein the biotin is bound to the nucleic acid, and a tamavidin-immobilized insoluble carrier to form a complex of the nucleic acid-binding protein, the biotinylated nucleic acid, and the tamavidin-immobilized insoluble carrier (step C-1),
   (2) a step for separating the biotinylated nucleic acid to which the nucleic acid-binding protein is bound from the complex obtained in the step C-1, in a solution having pH of 7.8 to 9.5, and in the presence of free biotin (step C-2),
   (3) a step for separating the nucleic acid-binding protein from the biotinylated nucleic acid to which the nucleic acid-binding protein is bound obtained in the step C-2 (step C-3).

8. The method according to claim 7, wherein the tamavidin is a tamavidin 2-REV.

9. The method according to claim 7, wherein the step C-1 is carried out in the presence of 40 to 4000 times mol of free biotin relative to the tamavidin.

10. A kit for separating a nucleic acid, comprising a reagent containing an insoluble carrier on which tamavidin is immobilized, and a reagent which makes pH of the solution after mixing in 7.8 to 9.5, as constituent reagents.

11. The kit according to claim 10, wherein the tamavidin is tamavidin 2-REV.

12. The kit according to claim 10, wherein the reagent which makes pH of the solution after mixing in 7.8 to 9.5 is a reagent that contains free biotin.

13. The kit according to claim 10, further comprising a reagent containing free biotin, as a constituent reagent.

* * * * *